(12) United States Patent
Zhang et al.

(10) Patent No.: US 11,931,030 B2
(45) Date of Patent: Mar. 19, 2024

(54) STAPLING DEVICE WITH CARTRIDGE ASSEMBLY WITH ALIGNMENT PINS

(71) Applicant: Covidien LP, Mansfield, MA (US)

(72) Inventors: Xini Zhang, Shanghai (CN); Syed Sarfraz Ahamed, Shanghai (CN); Jiangfeng Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/802,301

(22) PCT Filed: Feb. 26, 2020

(86) PCT No.: PCT/CN2020/076830
§ 371 (c)(1),
(2) Date: Aug. 25, 2022

(87) PCT Pub. No.: WO2021/168704
PCT Pub. Date: Sep. 2, 2021

(65) Prior Publication Data
US 2023/0094346 A1    Mar. 30, 2023

(51) Int. Cl.
*A61B 17/072*    (2006.01)
*A61B 17/00*    (2006.01)
*A61B 90/00*    (2016.01)

(52) U.S. Cl.
CPC .. *A61B 17/072* (2013.01); *A61B 2017/00384* (2013.01); *A61B 2017/00477* (2013.01); *A61B 2017/00871* (2013.01); *A61B 2017/07221* (2013.01); *A61B 2017/07257* (2013.01); *A61B 2017/07271* (2013.01); *A61B 2017/07285* (2013.01); *A61B 2090/038* (2016.02)

(58) Field of Classification Search
CPC ............... A61B 17/068; A61B 17/072; A61B 2017/07221; A61B 2017/07271
See application file for complete search history.

(56) References Cited

U.S. PATENT DOCUMENTS 5,706,998 A * 1/1998 Plyley ................. A61B 17/072
227/176.1
10,939,910 B2 * 3/2021 Maddur Shankarsetty ................
A61B 90/90

(Continued)

FOREIGN PATENT DOCUMENTS

CN    1669533 A    9/2005
CN    1669535 A    9/2005

(Continued)

OTHER PUBLICATIONS

International Search Report for Application No. PCT/CN2020/076830 dated Nov. 30, 2020.

(Continued)

*Primary Examiner* — Gloria R Weeks
(74) *Attorney, Agent, or Firm* — Carter, DeLuca & Farrell LLP

(57) ABSTRACT

A surgical stapling device includes an anvil assembly and a replaceable cartridge assembly. The cartridge assembly includes a knife blade and upper and lower alignment pins for retaining tissue between anvil and cartridge assemblies to ensure that the knife blade cuts cleanly through tissue. The cartridge assembly includes a cartridge body having guide structure for guiding the cartridge assembly onto a clamp slide assembly of the stapling device.

20 Claims, 17 Drawing Sheets

(56) References Cited

U.S. PATENT DOCUMENTS

| | | | |
|---|---|---|---|
| 11,744,584 B2* | 9/2023 | Maddur | A61B 17/072 227/180.1 |
| 2005/0139634 A1 | 6/2005 | Schwemberger et al. | |
| 2007/0039996 A1 | 2/2007 | Mather et al. | |
| 2012/0080473 A1 | 4/2012 | Farascioni et al. | |
| 2018/0153544 A1* | 6/2018 | Maddur Shankarsetty | A61B 90/90 |
| 2019/0000455 A1* | 1/2019 | Adams | A61B 17/072 |
| 2023/0052972 A1* | 2/2023 | Maddur | A61B 17/072 |

FOREIGN PATENT DOCUMENTS

| | | |
|---|---|---|
| CN | 201160869 Y | 12/2008 |
| CN | 202497184 U | 10/2012 |
| CN | 202619744 U | 12/2012 |
| CN | 208447681 U | 2/2019 |
| CN | 108430342 B | 7/2021 |
| EP | 3586769 B1 | 8/2021 |
| JP | 2005193033 A | 7/2005 |
| JP | 2008055165 A | 3/2008 |
| JP | 2010259792 | 11/2010 |
| JP | 3209123 U | 2/2017 |

OTHER PUBLICATIONS

Written Opinion for Application No. PCT/CN2020/076830 dated Nov. 30, 2020.
Extended European Search report dated Oct. 6, 2023, issued in corresponding EP Appln. No. 20921548, 10 pages.
Japanese Office Action dated Dec. 21, 2023, issued in corresponding Japanese Appln. No. 2022551285, 4 pages.

* cited by examiner

STAPLING DEVICE WITH CARTRIDGE ASSEMBLY WITH ALIGNMENT PINS

FIELD

This technology is generally related to surgical stapling devices and, more particularly, to surgical stapling devices with removable staple cartridges.

BACKGROUND

Surgical stapling devices are commonly used during a variety of surgical procedures to expedite dissection and suturing of tissue and minimize trauma to a patient. Typically, these stapling devices include a cartridge assembly that includes a staple cartridge that can be replaced after each use of the stapling device to facilitate reuse of the stapling device. These devices also include a knife assembly for cutting tissue and an anvil assembly that supports a cutting plate which is engaged by the knife assembly to provide a more effective cutting process. The knife assembly includes a knife blade that has a sharpened cutting edge which is driven through tissue and into the cutting plate to transect or resect the tissue. Typically, the replaceable cartridge assembly includes an alignment pin or alignment pins that confine tissue between the cartridge and anvil assemblies.

A continuing need exists in the art for a stapling device that includes a cartridge assembly including an alignment pin or alignment pins that confine the tissue between the anvil and cartridge assemblies to ensure that tissue is cleanly cut by the knife blade.

SUMMARY

Aspects of this disclosure are directed to a surgical stapling device including an elongate body, a clamp slide assembly, a tool assembly, and an alignment pin advancement assembly. The elongate body has a proximal portion and a distal portion. The tool assembly is supported on the distal portion of the elongate body and includes a U-shaped frame, an anvil assembly, and a reload assembly. The U-shaped frame has a first transverse portion, a second transverse portion, and a longitudinal portion that connects the first transverse portion to the second transverse portion. The second transverse portion defines at least one longitudinal slot. The anvil assembly is supported on the first transverse portion of the U-shaped frame and includes a staple deforming surface defining a knife slot and a lower opening. The reload assembly includes a cartridge assembly and a shipping cap. The cartridge assembly includes a cartridge body defining a cavity, a knife slot, and a plurality of staple pockets. The cartridge assembly further includes a tissue engaging surface, a plurality of staples positioned within the staple pockets, and a first alignment pin. The first alignment pin is movable from a retracted position positioned within the cartridge body to a fully advanced position extending from the cartridge body and into the lower opening defined in the anvil assembly. The shipping cap is supported on the cartridge body and includes a base member positioned on the tissue engaging surface of the cartridge body to prevent advancement of the first alignment pin and to retain the plurality of staples within the plurality of staple pockets. The clamp slide assembly includes a distal portion and a proximal portion. The distal portion defines a distal cartridge support. The clamp slide assembly is movable between a retracted position and an advanced position to move the cartridge assembly in relation to the anvil assembly between open and clamped positions. The alignment pin advancement assembly is supported on the second transverse portion of the U-shaped frame and includes a tube, at least one button, a shaft, and a biasing member. The tube is supported within the second transverse portion of the U-shaped frame for movement in relation to the second transverse portion between retracted and advanced positions. The shaft is supported within the tube for movement in relation to the tube between retracted and advanced positions. The biasing member is positioned within the tube to urge the shaft towards its advanced position. The at least one button extends through the at least one longitudinal slot defined within the second transverse portion of the U-shaped frame and is coupled to the tube. The at least one button is movable within the longitudinal slot from a retracted position to an advanced position to move the tube within the second transverse portion between its retracted and advanced positions. The shaft is aligned with the first alignment pin to urge the first alignment pin towards its advanced position.

Other aspects of the disclosure are directed to a surgical stapling device including an elongate body and a tool assembly. The elongate body has a proximal portion and a distal portion. The tool assembly is supported on the distal portion of the elongate body and includes a U-shaped frame, an anvil assembly, and a cartridge assembly. The U-shaped frame has a first transverse portion, a second transverse portion, and a longitudinal portion that connects the first transverse portion to the second transverse portion. The second transverse portion defines at least one longitudinal slot. The anvil assembly is supported on the first transverse portion of the U-shaped frame and includes a staple deforming surface defining a knife slot and a lower opening. The cartridge assembly includes a cartridge body having side walls with inner surfaces defining a cavity. The inner surfaces of the side walls define at least one longitudinal channel. The clamp slide assembly includes a distal portion and a proximal portion. The distal portion defines a distal cartridge support. The clamp slide assembly is movable between a retracted position and an advanced position to move the cartridge assembly in relation to the anvil assembly between open and clamped positions. The distal cartridge support of the clamp slide assembly has an outer surface that defines at least one guide member. The at least one longitudinal guide channel of the cartridge body receives the at least one guide member of the distal cartridge support during securement of the cartridge assembly to the distal cartridge support of the clamp slide assembly to properly align the cartridge assembly onto the distal cartridge support.

Other aspects of the disclosure are directed to a surgical stapling device including an elongate body and a tool assembly. The elongate body has a proximal portion and a distal portion. The tool assembly is supported on the distal portion of the elongate body and includes a U-shaped frame, an anvil assembly, a cartridge assembly, and a clamp slide assembly. The U-shaped frame has a first transverse portion, a second transverse portion, and a longitudinal portion that connects the first transverse portion to the second transverse portion. The anvil assembly is supported on the first transverse portion of the U-shaped frame and includes a staple deforming surface that defines a knife slot and a lower opening. The cartridge assembly includes a cartridge body having an alignment pin including an elongate shaft and an over mold supported about the elongate shaft. The alignment pin is movable from a retracted position positioned within the cartridge body to an advanced positon engaged with the anvil assembly. The clamp slide assembly includes a distal portion and a proximal portion. The distal portion defines a distal cartridge support that supports the cartridge assembly. The clamp slide assembly is movable between a retracted position and an advanced position to move the cartridge assembly in relation to the anvil assembly between open and clamped positions.

In aspects of the disclosure, the at least one longitudinal slot includes two longitudinal slots and the at least one button includes two buttons.

In some aspects of the disclosure, the shipping cap includes an engagement portion that is configured to releasably secure the shipping cap to the cartridge assembly, wherein the shipping cap is removable from the cartridge assembly to allow the shaft of the alignment pin advancement assembly to advance the first alignment pin from its retracted position to a partially advanced position in which the first alignment pin is spaced from the anvil assembly.

In certain aspects of the disclosure, the at least one button is movable within the at least one longitudinal slot to move the first alignment pin from the partially advanced position to the fully advanced position.

In aspects of the disclosure, the at least one longitudinal slot includes spaced protrusions, wherein one of the spaced protrusions is positioned to retain the at least one button in its retracted position in the at least one longitudinal slot and the other of the spaced protrusions is positioned to retain the button in its advanced position within the at least one longitudinal slot.

In some aspects of the disclosure, the stapling device includes a handle assembly, and the proximal portion of the elongate body is coupled to the handle assembly.

In certain aspects of the disclosure, the distal cartridge support of the clamp slide assembly includes an outer surface that defines at least one guide member, and the cartridge body includes side walls defining the cavity that include at least one longitudinal guide channel that receives the at least one guide member during securement of the cartridge assembly to the distal cartridge support of the clamp slide assembly to properly align the cartridge assembly on the distal cartridge support.

In aspects of the disclosure, the at least one guide member includes two guide members positioned on the outer surface of the distal cartridge support on each side of the distal cartridge support, and the at least one longitudinal guide channel includes two longitudinal guide channels defined on each of the side walls of the cartridge body.

In some aspects of the disclosure, the distal cartridge support of the clamp slide assembly includes at least one detent and the cartridge body defines at least one resilient leg and at least one recess, wherein the at least one resilient leg is deformable out of the path of the at least one detent to allow passage of the at least one detent into the at least one recess to secure the cartridge assembly to the distal cartridge support of the clamp slide assembly.

In certain aspects of the disclosure, the at least one detent includes a plurality of detents, the at least one resilient leg includes a plurality of resilient legs, and the at least one recess includes a plurality of recesses.

In aspects of the disclosure, the stapling device includes a second alignment pin spaced from the first alignment pin.

In some aspects of the disclosure, the second alignment pin includes an elongate shaft and an over mold supported about the elongate shaft, wherein the second alignment pin is movable from a retracted position positioned within the cartridge body to an advanced positon engaged with the anvil assembly.

In certain aspects of the disclosure, the elongate shaft of the second alignment pin is formed from metal and the over mold is formed from of a plastic or polymeric material.

In aspects of the disclosure, the over mold is formed from a silicon rubber.

Other features of the disclosure will be appreciated from the following description.

BRIEF DESCRIPTION OF THE DRAWINGS

Various aspects of the disclosure are described herein below with reference to the drawings, wherein.

DETAILED DESCRIPTION

Figure 1:
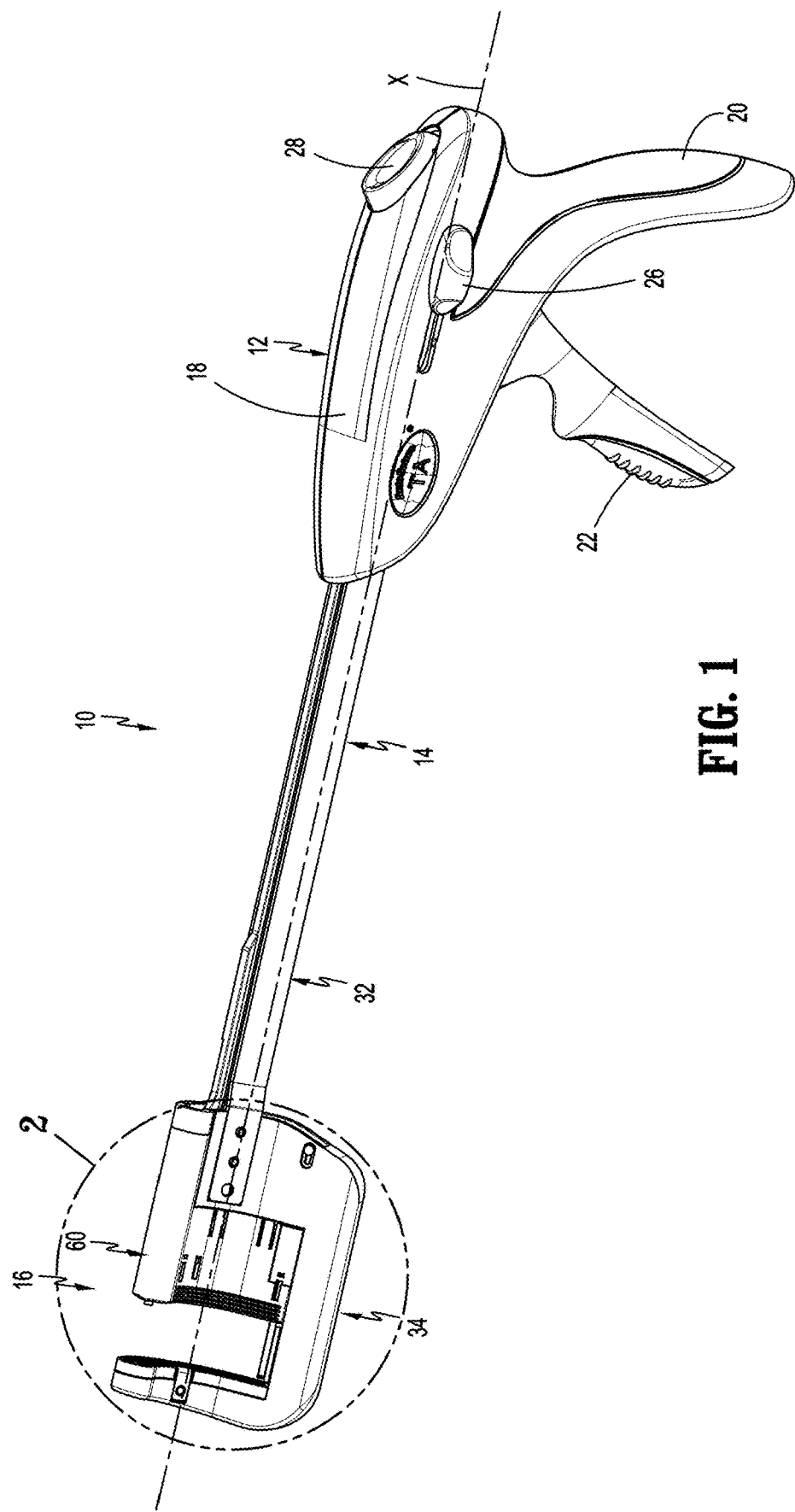
FIG. 1 is a side perspective view of a surgical stapling device including aspects of the disclosure.

The disclosed surgical stapling device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 2:
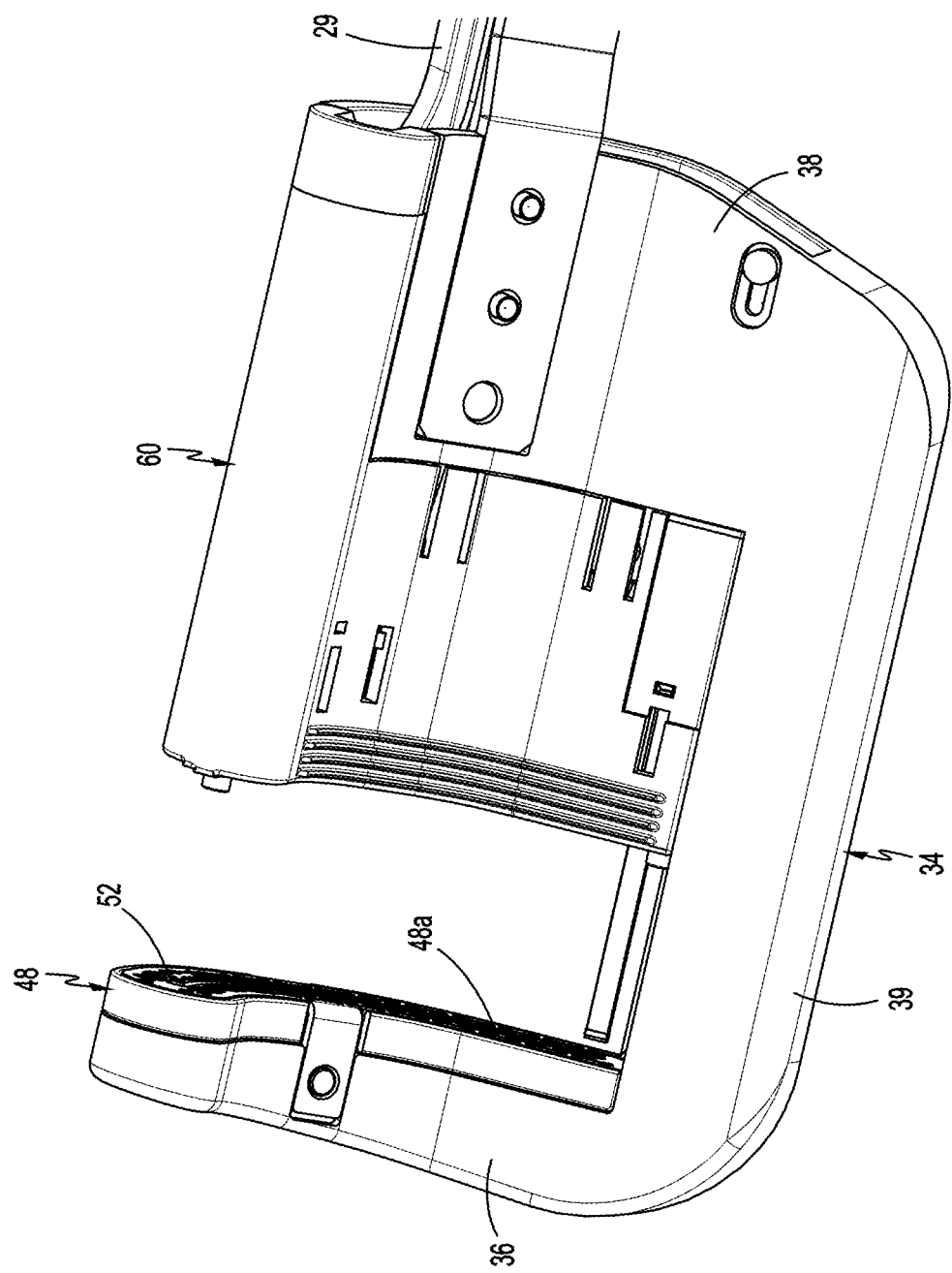
FIG. 2 is an enlarged view of the indicated area of detail shown in FIG. 1 illustrating a distal portion of the surgical stapling device in a pre-fired unclamped position.
Figure 3:
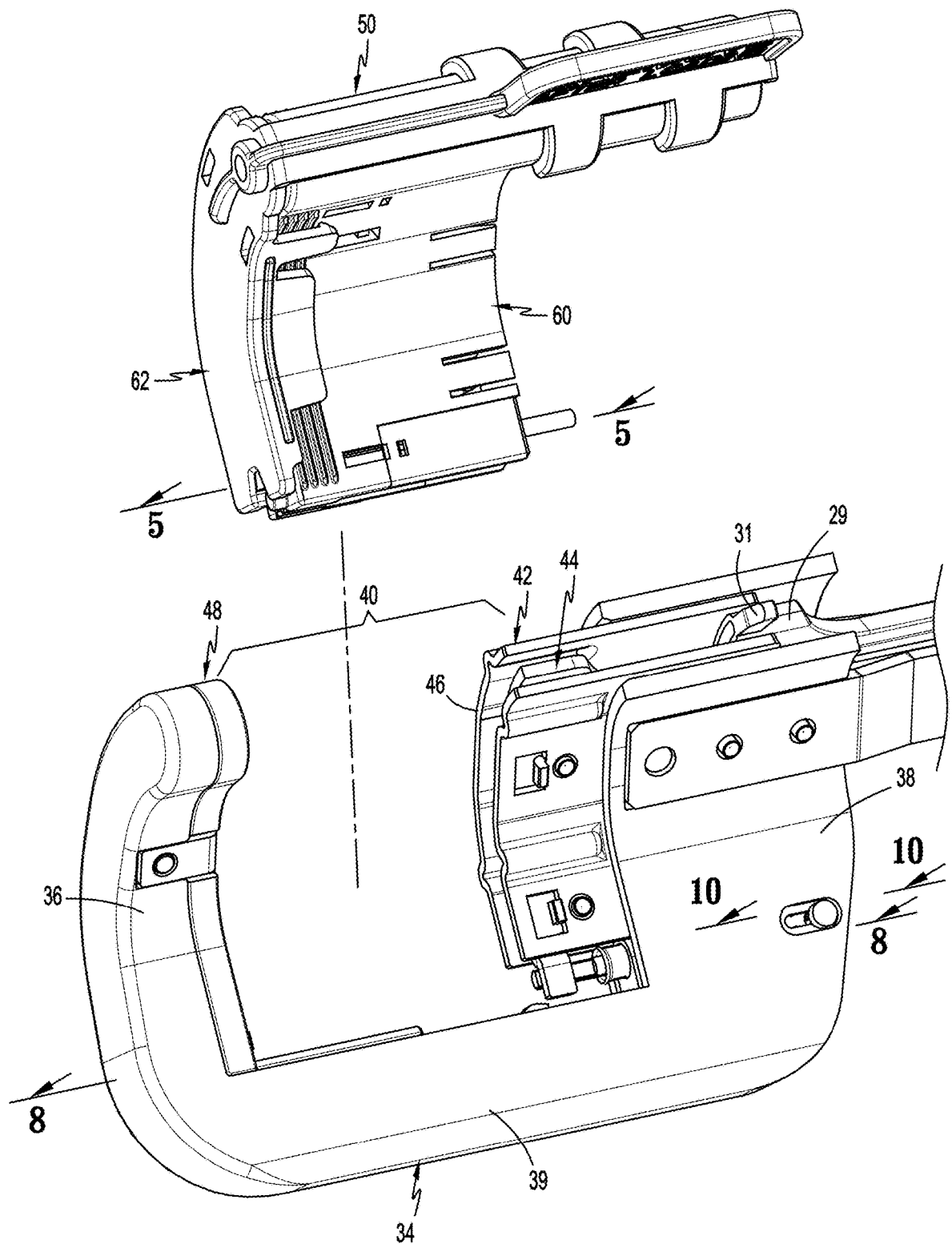
FIG. 3 is a side perspective view of the distal portion of the surgical stapling device shown in FIG. 1 illustrating a reload assembly of the stapling device shown in FIG. 1 separated from a clamp slide assembly of the surgical stapling device.

FIGS. 1-3 illustrate the disclosed surgical stapling device shown generally as stapling device 10. The stapling device 10 includes a handle assembly 12, an elongate body 14 that extends distally from the handle assembly 12, and a tool assembly 16 that is supported on a distal portion of the elongate body 14. The elongate body 14 defines a longitudinal axis "X". The handle assembly 12 includes a housing 18 that defines a stationary handle 20 and supports a movable trigger 22. In aspects of the disclosure, the movable trigger 22 is supported by the housing 18 to pivot towards the stationary handle 20 between non-actuated and actuated positions to operate the tool assembly 16. The handle assembly 12 also supports buttons 26 (only one is shown) positioned on each side of the housing 18 that are movable along the housing 18 to advance and retract an alignment pin pusher 29 (FIG. 3). The handle assembly 12 also includes a release button 28 that can be depressed to move the tool assembly 16 from a clamped position to an unclamped position. For a more detailed description of a suitable handle assembly 12, see, e.g., U.S. Pat. No. 6,817,508 ("the '508 patent").

The stapling device 10 includes a frame 32 that extends from the handle assembly 12 to the tool assembly 16. The frame 32 includes a distal frame portion 34 that has a U-shaped configuration. The distal frame portion 34 (FIG. 3) has a first transverse portion 36, a second transverse portion 38, and a longitudinal portion 39 that interconnects the first transverse portion 36 and the second transverse portion 38. The first and second transverse portions 36 and 38 are spaced from each other to define a gap 40 that extends between the first and second transverse portions 36 and 38. In some aspects of the disclosure, the first and second transverse portion 36 and 38 are curved along axes transverse to the longitudinal axis "X" of the elongate body 14 of the stapling device 10. Alternately, the first and second transverse portions 36 and 38 may be linear or comprised of a plurality of linear portions that are positioned at angles in relation to each other.

The stapling device 10 includes a clamp slide assembly 42 and a thrust bar 44. The clamp slide assembly 42 is formed of first and second clamp slide members 42a and 42b which are coupled together as described in further detail below to define a distal cartridge support 46 positioned within the gap 40 of the distal frame portion 34. The clamp slide assembly 42 has a proximal portion that is coupled to the handle assembly 12 and is movable between retracted and advanced positions in response to actuation of the movable trigger 22. The thrust bar 44 also includes a proximal portion that is coupled to the handle assembly 12 and is movable between retracted and advanced positions in response to actuation of the movable trigger 22.

Figure 17:
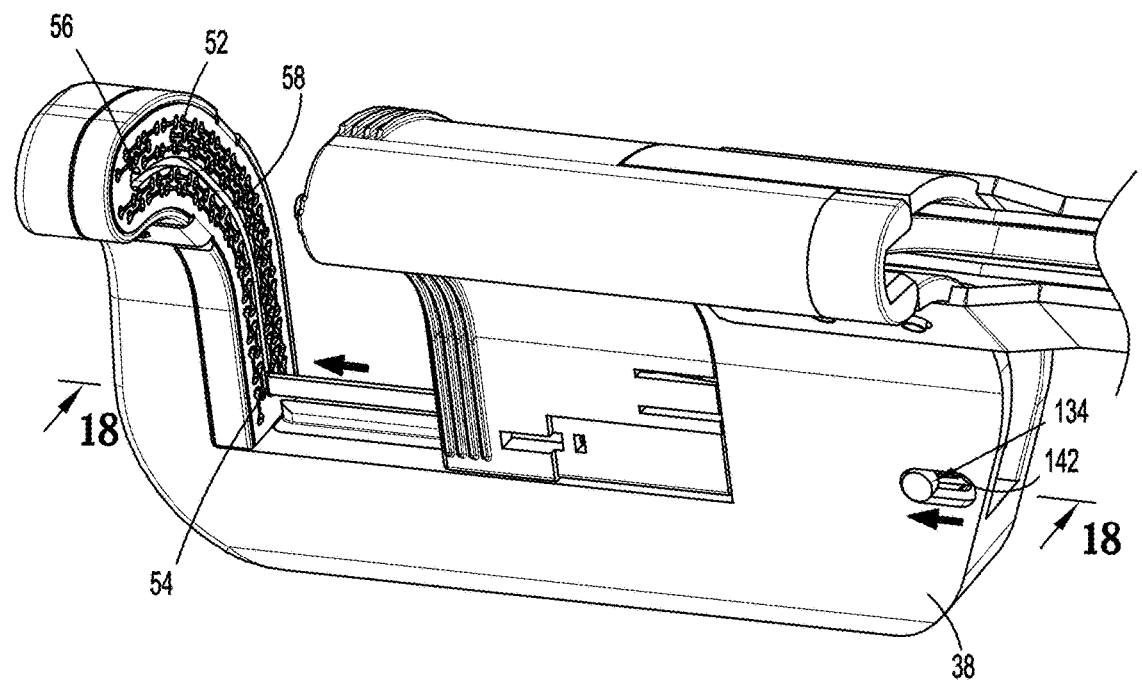
FIG. 17 is a side view of the distal portion of the stapling device shown in FIG. 1 with the reload assembly attached to the clamp slide assembly, a shipping cap removed from a cartridge assembly of the reload assembly, the lower pin advancement assembly in a fully advanced position, and the stapling device in an unclamped position.

The tool assembly 16 includes an anvil assembly 48 and a reload assembly 50. The anvil assembly 48 is secured to the first transverse portion 36 of the distal frame portion 34 and includes an anvil 48a having a staple deforming surface 52 (FIG. 17). The staple deforming surface 52 defines a lower opening 54, an upper opening 56, and a knife slot 58 that extends between the lower and upper openings 54 and 56, respectively.

Figure 4:
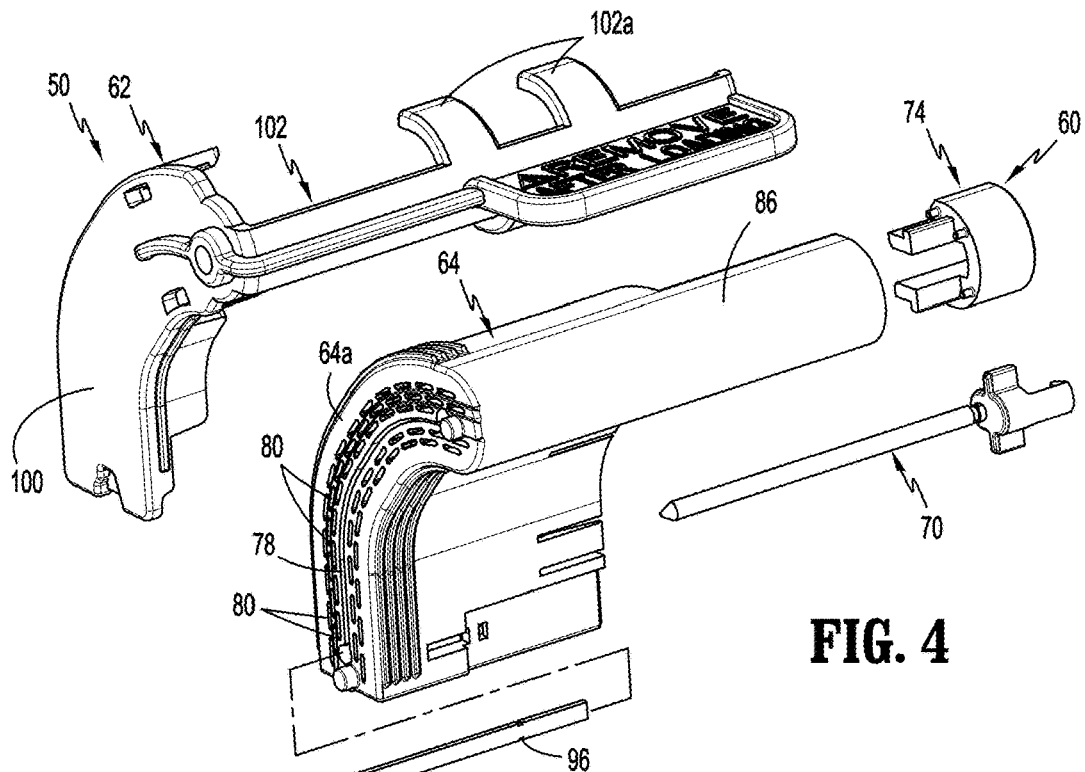
FIG. 4 is a side perspective, exploded view of the reload assembly shown in FIG. 3.
Figure 5:
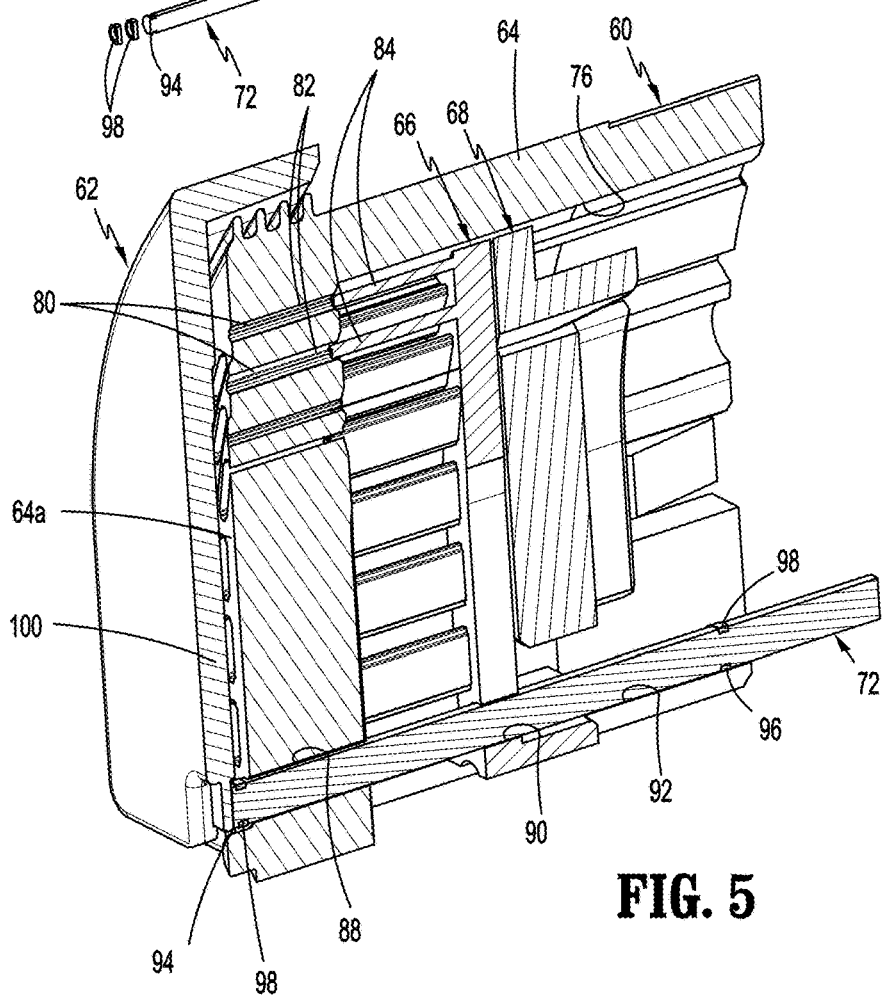
FIG. 5 is a cross-sectional view taken along section line 5-5 of FIG. 3.
Figure 6:
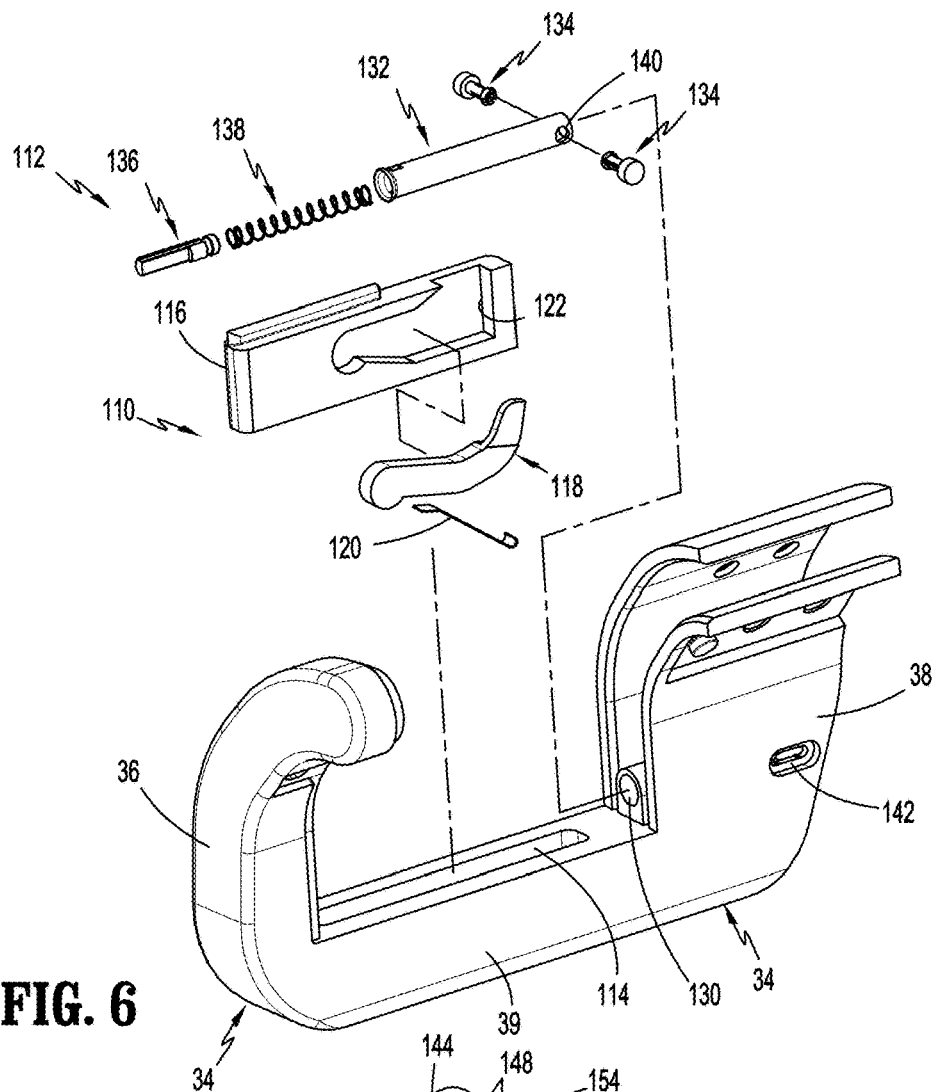
FIG. 6 is a side perspective, exploded view of the a distal frame portion, lockout assembly, and lower pin advancement assembly of the surgical stapling device shown in FIG. 1.

FIGS. 3-5 illustrate the reload assembly 50 which includes a cartridge assembly 60 and a shipping cap 62. The cartridge assembly 60 is removably supported on a clamp slide assembly 42 and includes a cartridge body 64, a staple pusher 66 (FIG. 5), a knife holder 68 (FIG. 5), an upper alignment pin 70, a lower alignment pin 72, and an upper alignment cap 74. The cartridge body 64 defines a cavity 76 (FIG. 5), a tissue engaging surface 64a, a knife slot 78, a plurality of staple pockets 80, and a plurality of staples 82. The knife slot 78 and the staple pockets 80 extend through the tissue engaging surface 64a and communicate with the cavity 76. The cavity 76 receives the staple pusher 66 and the knife holder 68 for movement between retracted and advanced positions. The staple pusher 66 includes fingers 84 that are received within the staple pockets 80 such that movement of the staple pusher 80 from its retracted position to its advanced position ejects the staples 82 from the staple pockets 80. The cartridge assembly 60 includes a knife blade (not shown) that is aligned with the knife slot 78 (FIG. 4) and is movable from a retracted positon shielded within the cartridge body 64 to an advanced position projecting from the knife slot 78 in response to movement of the knife holder 68 from its retracted position to its advanced position.

The cartridge body 64 includes proximal extension 86 that receives the upper alignment pin 70. The cartridge body 64 also defines a through bore 88 (FIG. 5) that receives the lower alignment pin 72. The through bore 88 is aligned with openings 90 and 92 formed in the staple pusher 66 and knife holder 68 such that the lower alignment pin 72 extends through the cartridge body 64 along an axis that is parallel to the longitudinal axis "X" of the elongate body 14 (FIG. 1) of the stapling device 10. The lower alignment pin 72 defines a distal groove 94 and a proximal groove 96. Each of the grooves 94 and 96 receives a flexible gasket or ring 98. The rings 98 are secure to the lower alignment pin 72 and are dimensioned to engage the cartridge body 64 to prevent the lower alignment pin 72 from falling from or becoming disengaged from the cartridge body 64.

The shipping cap 62 is releasably coupled to the cartridge assembly 60 and includes a base member 100 and a proximally extending engagement member 102. The base member 100 has a configuration that corresponds to the configuration of the cartridge body 64 and is received over the tissue engaging surface 64a. The engagement member 102 includes resilient C-clips 102a that receive the proximal extension 86 of the cartridge body 64 to secure the shipping cap 62 to the cartridge body 64. The shipping cap 62 is secured to the cartridge body 64 until the cartridge assembly 60 is secured to the clamp slide member 42 (FIG. 3) of the stapling device 10 (FIG. 1) immediately prior to use to prevent the staples 82 (FIG. 5) from falling from the cartridge body 64 prior to use. The shipping cap 62 also retains the lower alignment pin 72 in a retracted position within the cartridge body 64 until the shipping cap 62 is removed from the cartridge body 64.

FIGS. 6-10 illustrate the distal portion of the stapling device 10 (FIG. 1) which includes a distal frame portion 34 of the surgical stapling device 10 (FIG. 1), a lockout assembly 110, and a lower pin advancement assembly 112. The longitudinal portion 39 of the distal frame portion 34 defines a recess 114 that receives the lockout assembly 110. The lockout assembly 110 includes a base member 116, a lockout member 118, and a biasing member 120. The base member 116 is received within the recess 114 of the longitudinal portion 39 of the distal frame portion 34 and defines a cutout 122. The lockout member 118 is supported within the cutout 122 and is movable from a first position obstructing distal movement of the thrust bar 44 (FIG. 3) to a second position located within the cutout 122 allowing for distal movement of the thrust bar 44. For a more detailed description of the operation of an exemplary lockout assembly, see, e.g. the '508 patent.

Figure 7:
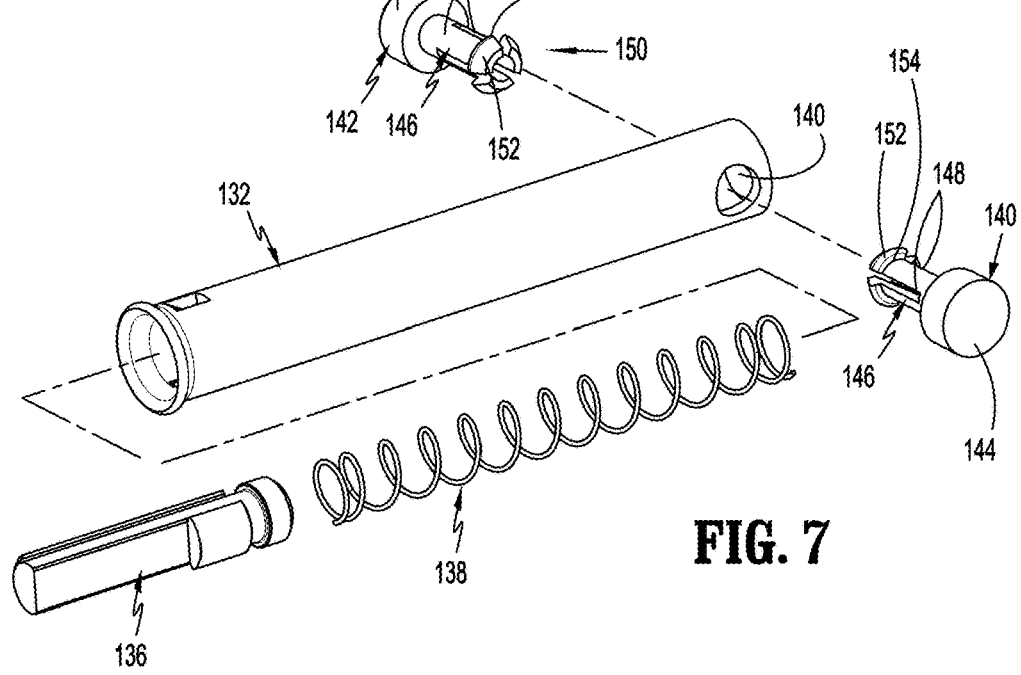
FIG. 7 is an enlarged perspective view of the lower pin advancement assembly shown in FIG. 6.
Figure 8:
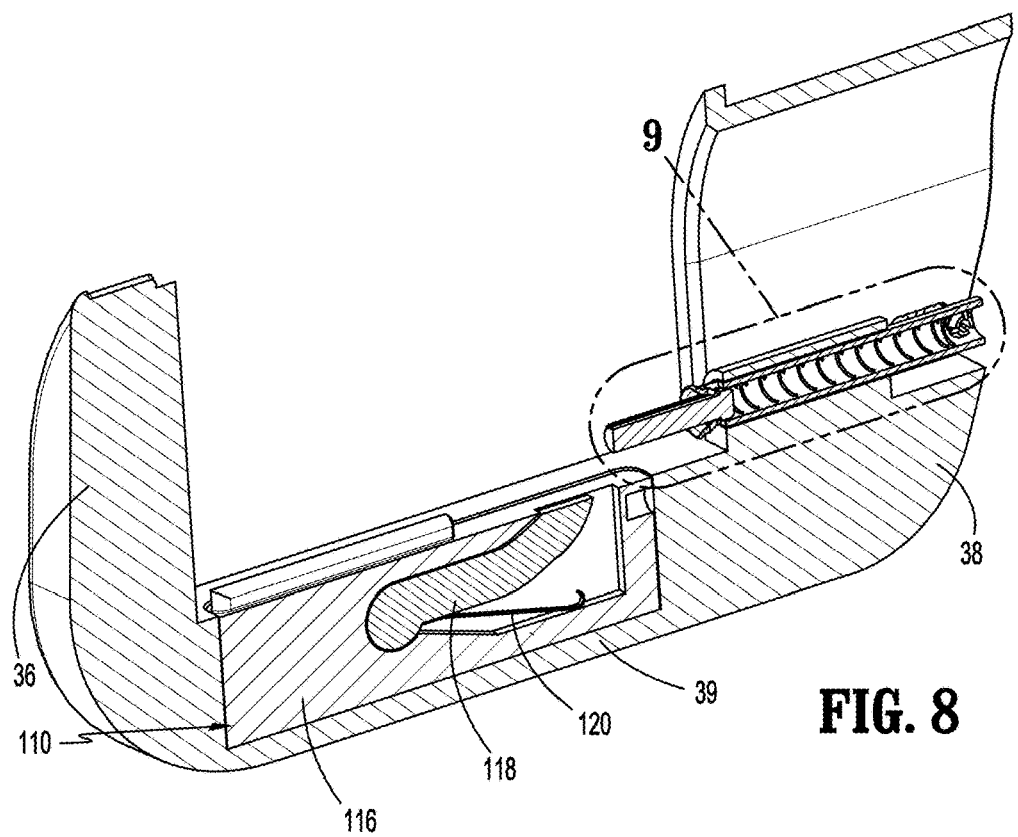
FIG. 8 is a cross-sectional view taken along section line 8-8 of FIG. 3.
Figure 9:
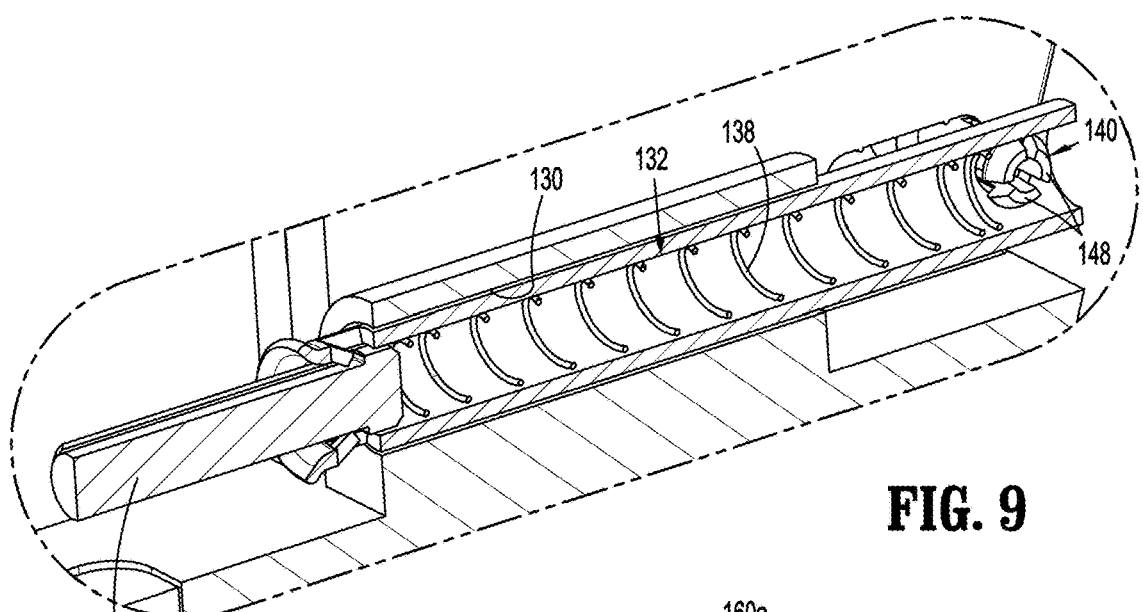
FIG. 9 is an enlarged view of the area of detail shown in FIG. 8.
Figure 18:
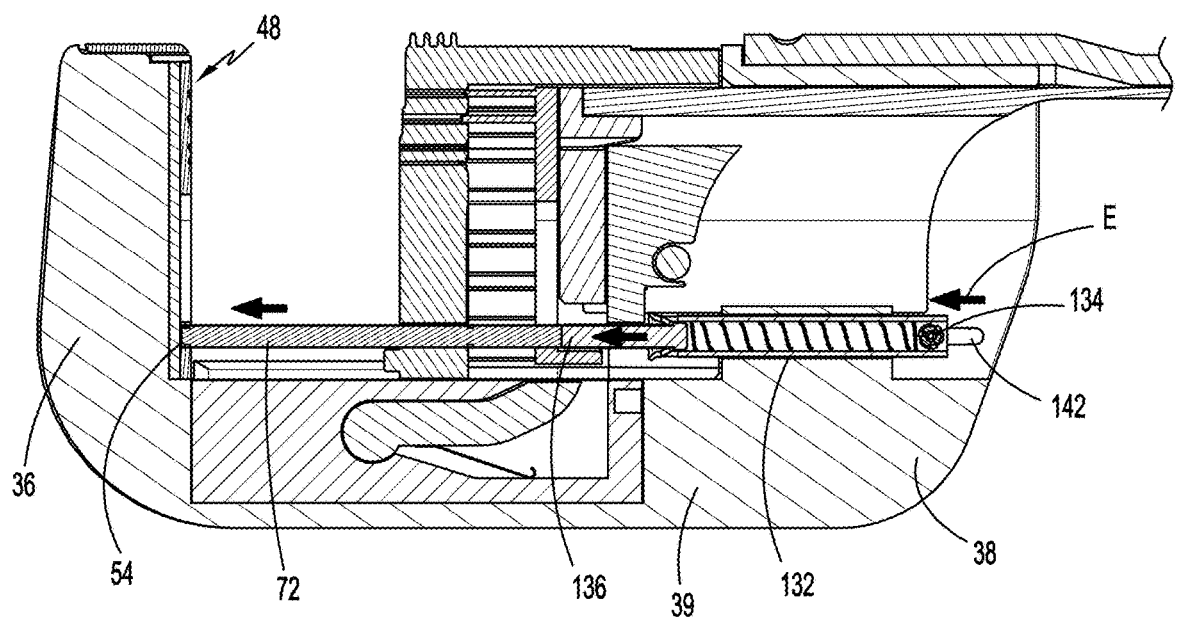
FIG. 18 is a cross-sectional view taken along section line 18-18 of FIG. 17 with the advancement lower pin assembly in the fully advanced position.
Figure 19:
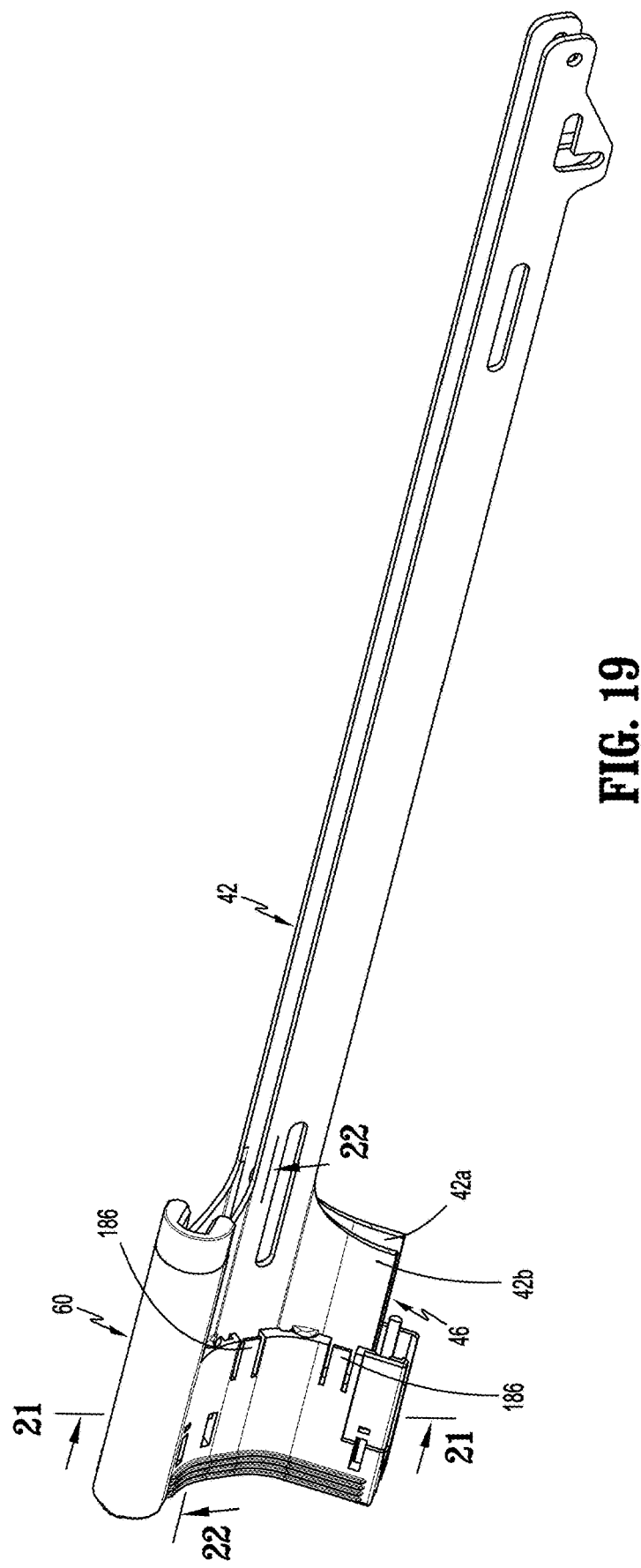
FIG. 19 is a side perspective view of the cartridge assembly of the reload assembly of the surgical stapling device shown in FIG. 1 supported on the distal portion of the clamp slide assembly.
Figure 20:
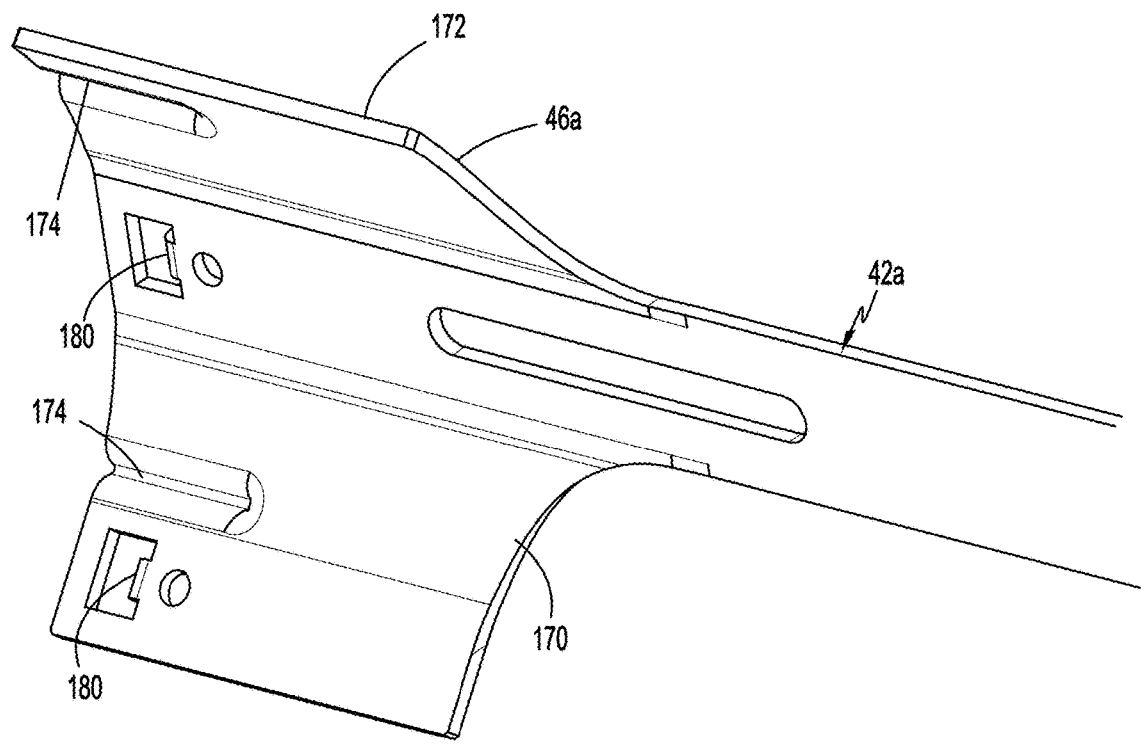
FIG. 20 is a side perspective view of the clamp slide assembly shown in FIG. 19 with clamp slide members separated.
Figure 20:
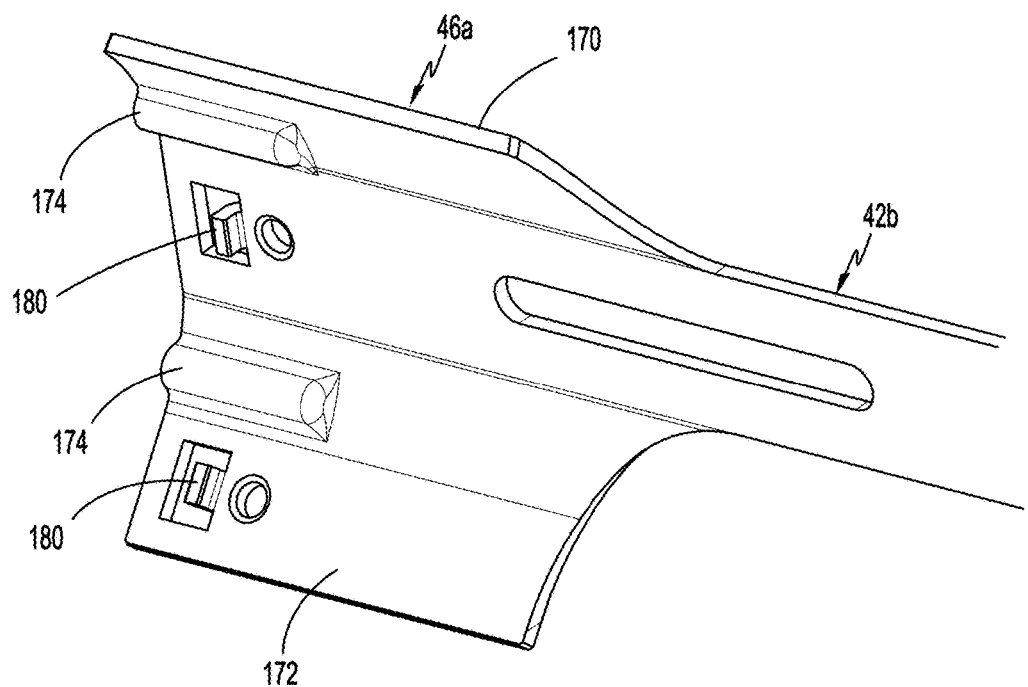
Figure 21:
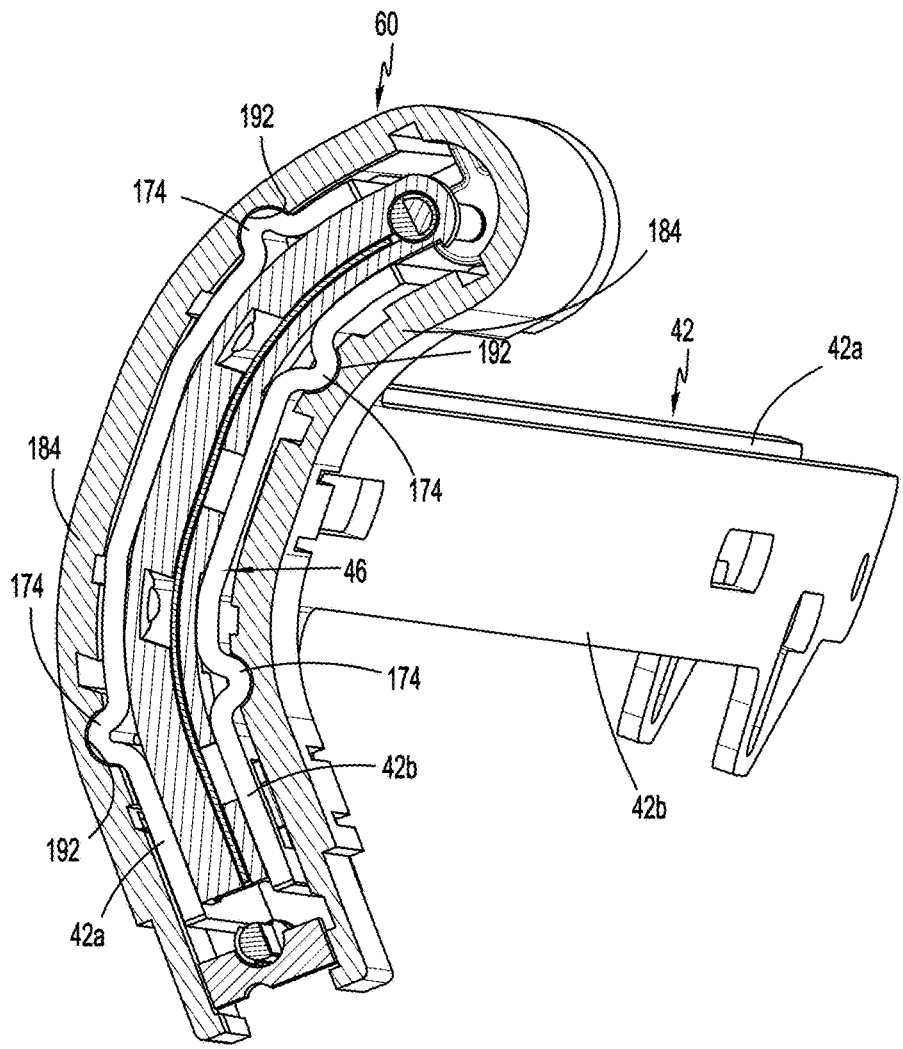
FIG. 21 is cross-sectional view taken along section line 21-21 of FIG. 19.
Figure 22:
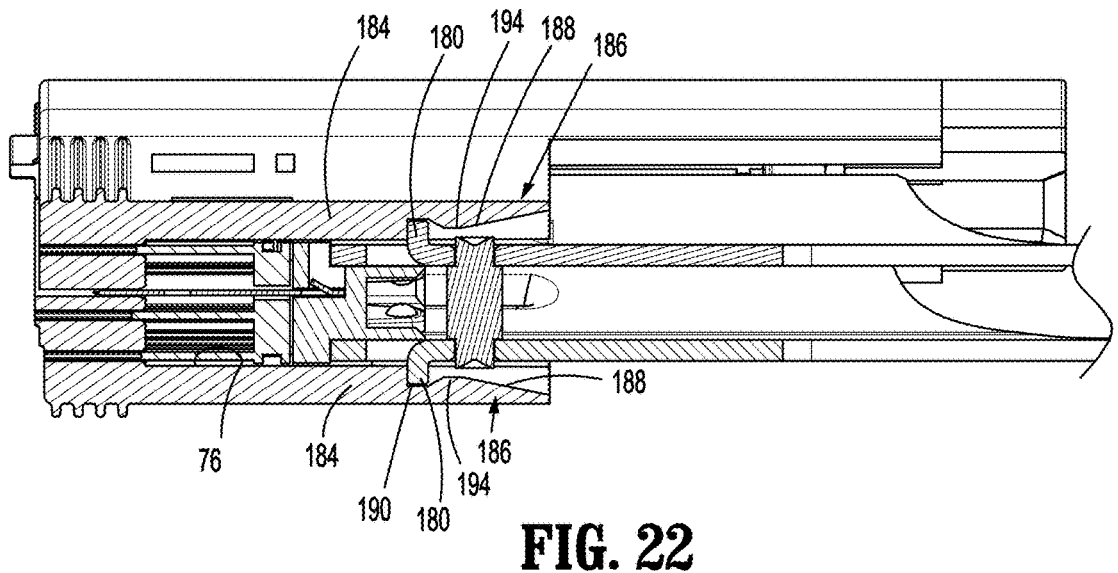
FIG. 22 is cross-sectional view taken along section line 22-22 of FIG. 19.

The lower pin advancement assembly 112 is supported in a cylindrical bore 130 (FIG. 6) defined in the second transverse portion 38 of the distal frame portion 34 and includes a tube 132, at least one button 134 (two are shown), a shaft 136, and a biasing member 138. The tube 132 is received within the cylindrical bore 130 and is movable from a retracted position (FIG. 14) to a partially advanced position (FIG. 16), to a fully advanced position (FIG. 18). The tube 132 includes a proximal portion that defines transverse through bores 140. The second transverse portion 38 of the distal frame portion 34 defines longitudinal slots 142 that are aligned with the through bores 140 in the tube 132. The buttons 134 extend through the slots 142 into the through bores 140 to secure the tube 132 to the buttons. Each of the buttons 134 includes a head portion 144 and a shaft portion 146 defined in part by resilient legs 148 (FIG. 7). The resilient legs 148 have end portions 150 that include a tapered surface 152 and a shoulder that defines a stop surface 154. The resilient legs 148 are deformable inwardly to facilitate passage of the legs 148 through the slots 142 in the distal frame portion 34 and the through bores 140 in the tube 132 to connect the buttons 134 to the tube 132. When the stop surface 154 of the legs 148 of the buttons 134 passes through the through bores 140 of the tube 132, the legs 148 snap back to their undeformed configurations to secure the resilient legs 148 within the tube 132. In the secured position, the stop surfaces 154 are engaged with an inner surface of the tube 132. The diameter of the shaft portions 146 (FIG. 7) of the buttons 134 is smaller than the length of the slots 142. As such, the buttons 134 are slidable through the slots 142 to move the tube 132 longitudinally within the cylindrical bore 130 of the second transverse portion 38 of the distal frame portion 34 between its retracted and advanced positions.

Figure 10:
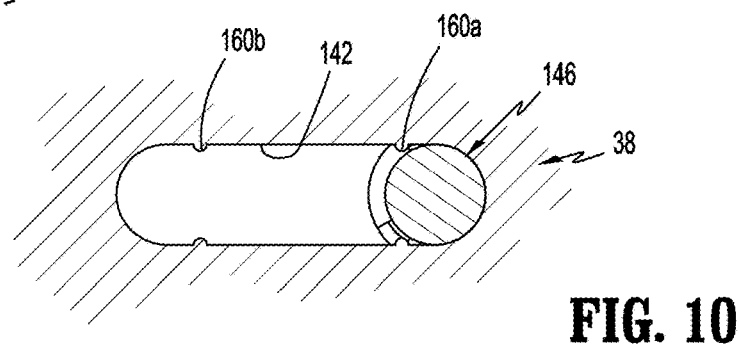
FIG. 10 is a cross-sectional view taken along section line 10-10 of FIG. 3.

The slots 142 in the second transverse portion 38 of the distal frame portion 34 each include spaced protrusions 160a and 160b (FIG. 10). The protrusions 160a and 160b are positioned to engage the shafts 146 of the buttons 134 to secure the buttons 134 within the slots 142 in either a retracted position or advanced position. More specifically, the protrusions 160a in the slots 142 of the second transverse portion 38 of the distal frame portion 34 engage the shafts 146 of the buttons 142 when the buttons 142 are in their retracted positions to retain the buttons 142 and the tube 132 in their retracted positions. Similarly, the protrusions 160b in the slots 142 of the second transverse portion 38 of the distal frame portion 34 engage the shaft 146 of the buttons 142 when the buttons 142 are in their advanced positions to retain the buttons 142 and the tube 132 in their advanced positions The biasing member 138 which is illustrated as a coil spring is positioned within the tube 132 (FIG. 9) and includes a proximal end that is engaged with the shafts 146 of the buttons 142 and a distal end that is engaged with the shaft 136 of the lower pin advancement assembly 112. The biasing member 138 is supported in compression and urges the shaft 136 of the lower pin advancement assembly 112 towards an advanced position within the tube 132.

Figure 11:
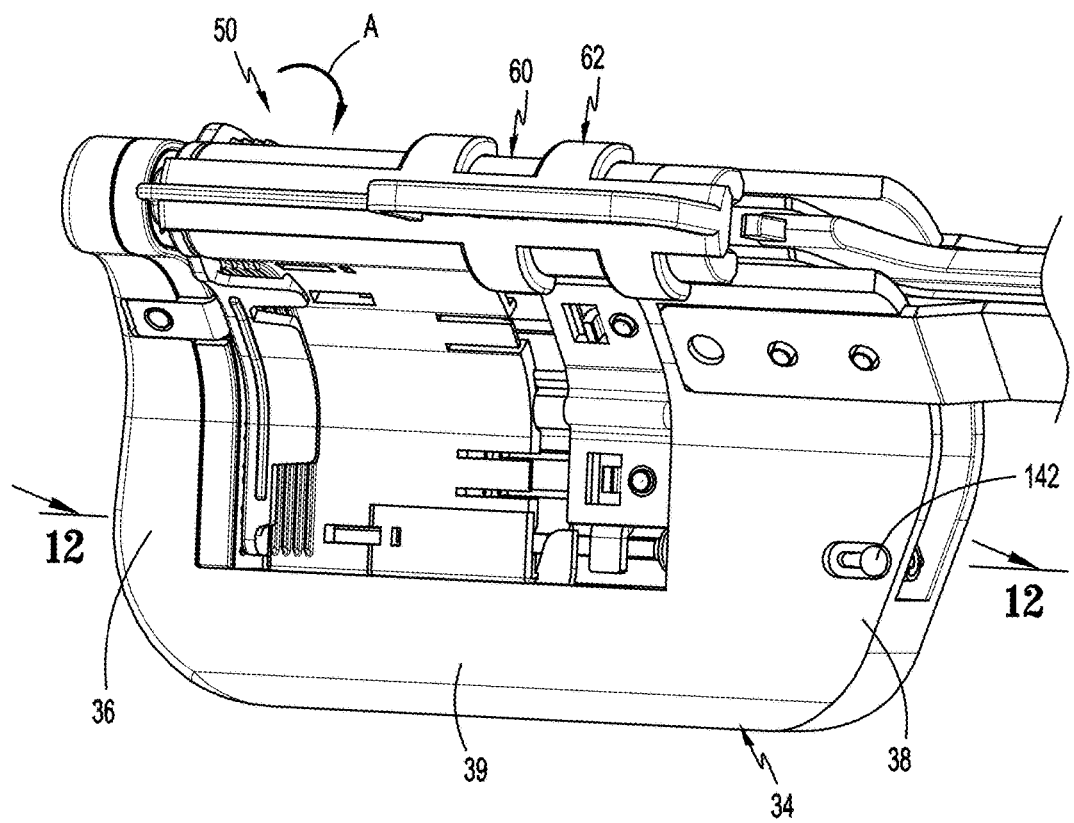
FIG. 11 is a side perspective view of the distal portion of the surgical stapling device shown in FIG. 1 as the reload assembly is attached to the clamp slide assembly.
Figure 12:
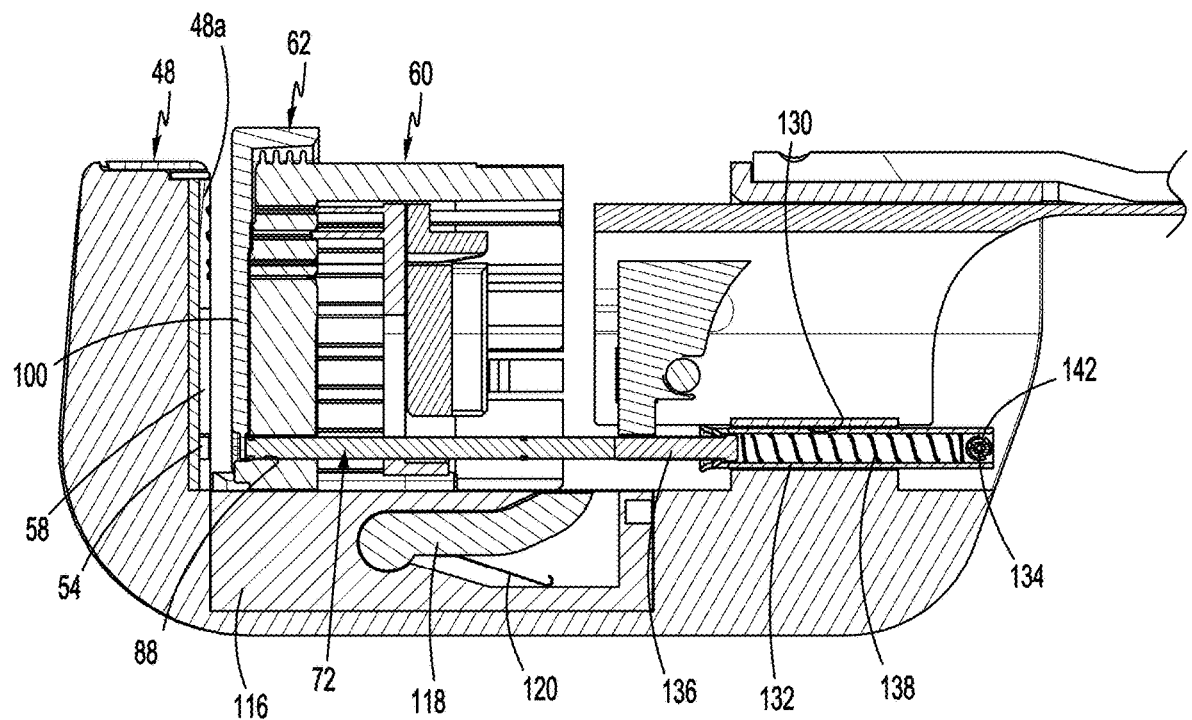
FIG. 12 is a cross-sectional view taken along section line 12-12 of FIG. 11.

FIGS. 11 and 12 illustrate the reload assembly 50 as the reload assembly 50 is secured to the clamp slide assembly 42 of the stapling device 10. As described above, the reload assembly 50 includes the cartridge assembly 60 and the shipping cap 62. When the shipping cap 62 is secured to the cartridge assembly 60, the base member 100 of the shipping cap 62 is received over the tissue engaging surface 64a of the cartridge body 64. In this position, the shipping cap 62 is positioned over the open distal end of the through bore 88 in the cartridge body 64 to prevent movement of the lower alignment pin 72 to its advanced position.

The reload assembly 50 is coupled to the clamp slide assembly 42 (FIG. 3) by first moving the cartridge body 64 along a transverse axis in the direction of arrow "A" in FIG. 12 to a position between the first and second transverse portions 36 and 38 of the distal frame portion 34 and subsequently sliding the reload assembly 50 proximally along the longitudinal axis "X" of the elongate body 14 in the direction of arrows "B" in FIGS. 13 and 14. When the reload assembly 50 is moved transversely in the direction of arrow "A" to the position between the first and second transverse portions 36 and 38 of the distal frame portion 34, the lower alignment pin 72 is moved into alignment with the shaft 136 of the lower pin advancement assembly 112. As the reload assembly 50 is slid longitudinally onto the clamp slide assembly 42 (FIG. 14), engagement between a proximal end of the lower alignment pin 72 and the shaft 136 of the lower pin advancement assembly 112 moves the shaft 136 proximally in the direction of arrow "C" in FIG. 14 to its retracted position. This movement compresses the biasing member 138 within the tube 132 of the lower pin advancement assembly 112. As described above, the shipping cap 62 prevents distal movement of the lower alignment pin 72 from the through bore 88 in the cartridge body 64.

Figure 15:
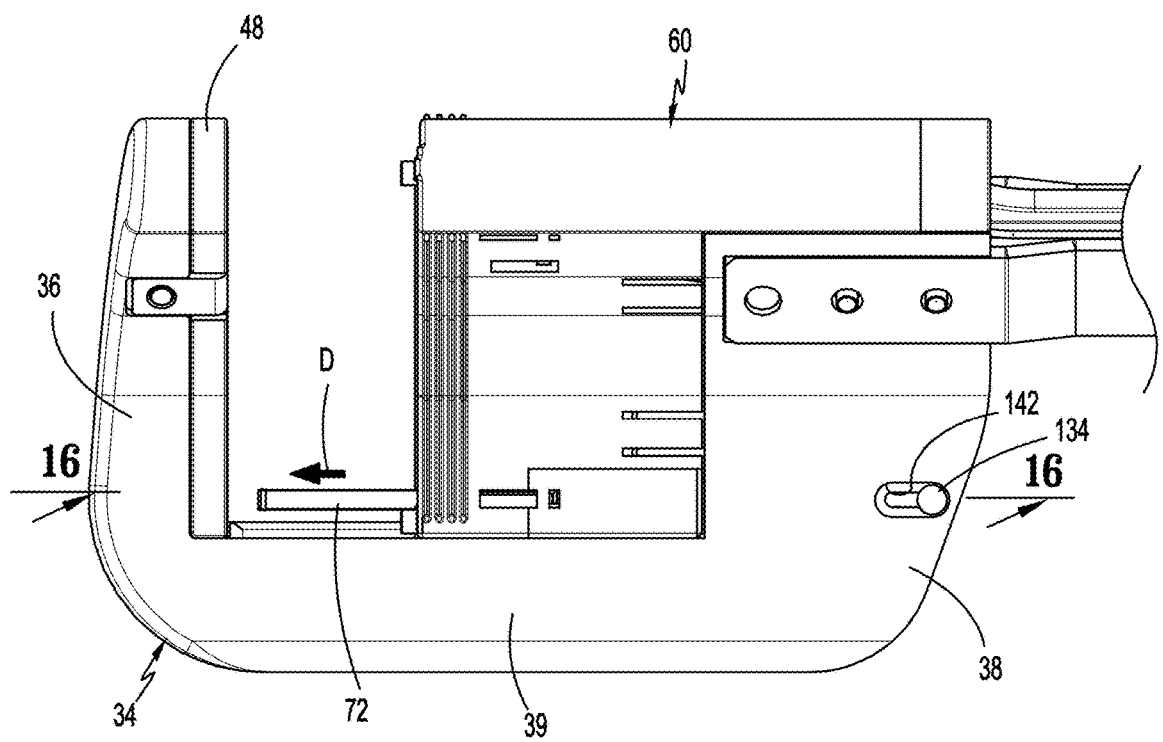
FIG. 15 is a side view of the distal portion of the stapling device shown in FIG. 1 with the reload assembly attached to the clamp slide assembly, a shipping cap removed from a cartridge assembly of the reload assembly, the lower pin advancement assembly in a partially advanced position, and the stapling device in an unclamped position.
Figure 16:
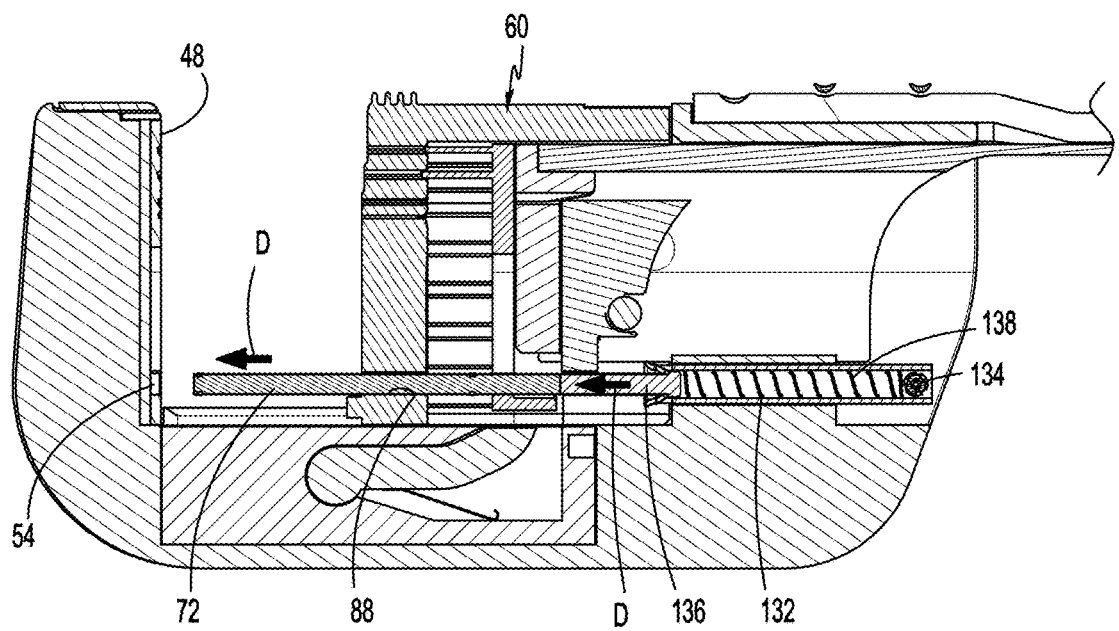
FIG. 16 is cross-sectional view taken along section line 16-16 of FIG. 13.

FIGS. 15 and 16 illustrate operation of the lower pin advancement assembly 112 after the shipping cap 62 is removed from the cartridge assembly 60. When the shipping cap 62 is removed from the cartridge assembly 60, the lower alignment 72 is now free to move distally in the direction of arrows "D". As described above, the shaft 136 of the lower pin advancement assembly 112 is engaged with the proximal end of the lower alignment pin 72. When the shipping cap 62 is removed from the cartridge assembly 60, the biasing member 138 expands within the tube 132 to advance the shaft 136 of the lower pin advancement assembly 112 in the direction of arrows "D" to its advanced position extending from the distal end of the tube 132. As the shaft 136 moves distally, the lower alignment pin 72 is moved distally from the within through bore 88 in the cartridge body 64 towards the lower opening 54 in the anvil assembly 48. The length of the biasing member 138 and the shaft 136 with the tube 132 in its retracted position is such that the lower alignment pin 72 will only move to a partially advanced position (FIG. 16) in which the lower alignment pin 72 is spaced from the opening 54 in the anvil assembly 48.

FIGS. 17 and 18 illustrate the tool assembly 16 as the lower alignment pin 72 is moved from the partially advanced position to its fully advanced position. In order to move the lower alignment pin 72 from the partially advanced position to the fully advanced position in which the lower alignment pin 72 is received within the lower opening 54 in the anvil assembly 48, the buttons 134 of the lower pin advancement assembly 112 are manually advanced from their retracted positions (FIG. 15) to their advanced positions (FIG. 17) in the direction of arrows "E" along the slots 142 formed in the second transverse portion 38. Advancement of the buttons 136 of the lower pin advancement assembly 112 moves the tube 132 of the lower pin advancement assembly 112 distally within the cylindrical bore 130 (FIG. 18) defined in the second transverse portion 38 of the distal frame portion 34 to advance the shaft 136 towards the anvil assembly 48. Advancement of the shaft 136 of the lower pin advancement assembly 112 advances the lower alignment pin 72 into the lower opening 54 in the anvil assembly 48. In the advanced position, the lower alignment pin 72 (in combination with the upper alignment pin 70) traps tissue between the anvil assembly 48 and the cartridge assembly 60 in the path of a knife blade (not shown) to ensure that the tissue is cleanly cut when the stapling device 10 (FIG. 1) is fired.

FIGS. 19-22 illustrate the clamp slide assembly 42 and the cartridge assembly 60 of the stapling device 10. As described above, the clamp slide assembly 42 includes first and second clamp slide members 42a and 42b which are coupled together to define a distal cartridge support 46 that is positioned within the gap 40 (FIG. 3) of the distal frame portion 34. The clamp slide members 42a and 42b can be coupled or secured together using rivets or the like. The clamp slide assembly 42 has a proximal portion that is coupled to the handle assembly 12 and is movable between retracted and advanced positions in response to actuation of the movable trigger 22. For a more detailed description of exemplary aspects of the proximal portion of the clamp slide members 42a and 42b and how the clamp slide members 42a and 42b may be associated with the handle assembly 12 (FIG. 1), see the '508 patent.

Each of the clamp slide members 42a and 42b has a distal portion 46a that collectively form the distal cartridge support 46 of the clamp slide assembly 42. The distal portion 46a of each of the clamp slide members 42a and 42b includes an inner surface 170 and an outer surface 172. The outer surface 172 of the clamp slide members 42a and 42b includes elongated guide members 174 that are define axes that are parallel to the longitudinal axis of the elongate body 14 (FIG. 1) of the stapling device 10. In aspects of the disclosure, the guide members 174 include two guide members 174 which are formed integrally with the clamp slide members 42a and 42b and are formed as raised elongated protrusions. Alternately, the guide members 174 could include one or more guide members 174 that are integrally with or separately from the clamp slide members 42a and 42b.

Each of the clamp slide members 42a and 42b also includes detents 180 that extend outwardly of the outer surface 172 of the clamp slide members 42a and 42b. The detents are positioned to engage the cartridge body 64 of the cartridge assembly 60 as described below to secure the cartridge assembly 60 onto the distal cartridge support 46 of the clamp slide assembly 42.

The cartridge body 64 of the cartridge assembly 60 includes side walls 184 that define the cavity 76 of the cartridge body 64. Each of the side walls 184 includes one or more resilient legs 186 that is secured to the cartridge body 64 in cantilevered fashion and is aligned with a respective one of the detents 180 of the clamp members 42a and 42b when the reload assembly 50 is secured to the distal cartridge support 46 of the clamp slide assembly 42. Each of the resilient legs 186 includes a tapered proximal portion 188 and a recess 190 positioned distally of the tapered proximal portion 188. An inner surface of the side walls 184 also defines longitudinal guide channels 192 that receive the guide members 174 of the clamp slide members 42a and 42b to guide the cartridge assembly 60 onto the distal cartridge support 46 of the clamp slide assembly 42.

Figure 13:
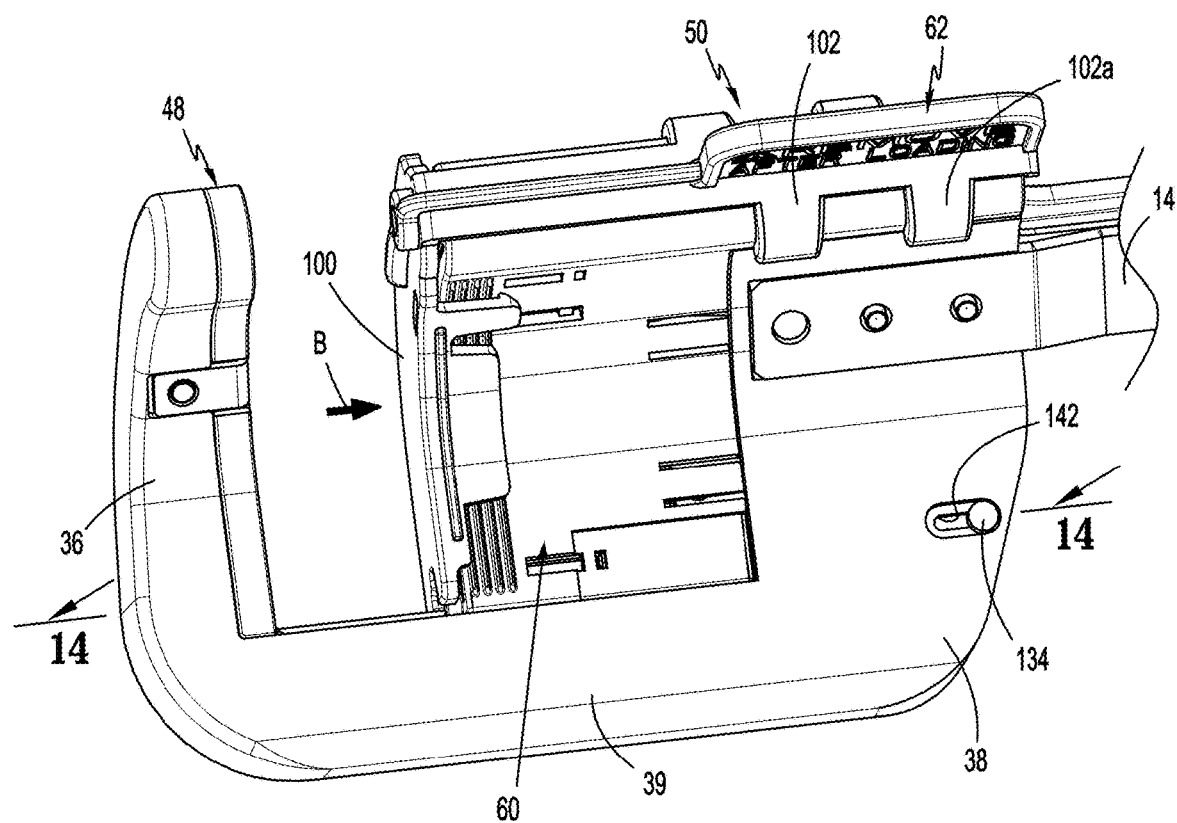
FIG. 13 is a side perspective view of the distal portion of the surgical stapling device shown in FIG. 1 as the reload assembly is attached to the clamp slide assembly during a first attachment step.
Figure 14:
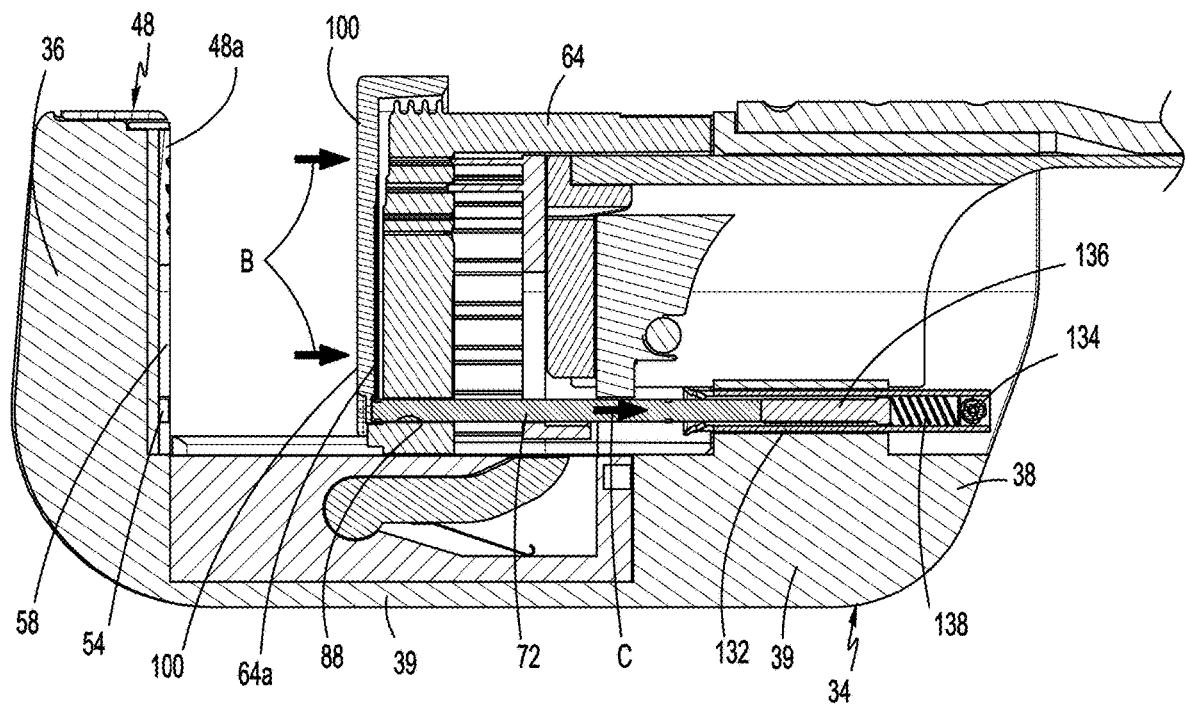
FIG. 14 is a cross-sectional view taken along section line 14-14 of FIG. 13.

When the reload assembly 50 is secured to the distal cartridge support 46 of the clamp slide assembly 42, and the cartridge assembly 60 is moved longitudinally towards the clamp slide assembly 42 as shown in FIGS. 13 and 14, the guide members 174 on the outer surfaces 172 of the clamp slide members 42a and 42b are received within the channels 192 on the inner surfaces of the side walls 184 of the cartridge body 64 to guide the cartridge assembly 60 onto the distal cartridge support 46 of the clamp slide assembly 42. When the resilient legs 186 engage the detents 180 of the clamp slide members 42a and 42b, the resilient legs 186 are deformed outwardly to allow the reload assembly 50 to be engaged with the clamp slide assembly 42 by passing the detents 180 beyond the highest point 194 (FIG. 22) of the resilient legs 186. When the detents 180 pass beyond the highest point of the resilient legs 186, the resilient legs 186 return to their original position such that the detents 180 move into the recesses 190 of the resilient legs 186.

FIGS. 23-29 illustrate an alternate version of the cartridge assembly shown generally as cartridge assembly 260. The cartridge assembly 260 is substantially identical to the cartridge assembly 60 (FIG. 3) except that the upper alignment pin 270 of the cartridge assembly 260 includes an over mold 276 as described below.

The upper alignment pin 270 includes an elongate pin shaft 272, a proximal coupling 274, and an over mold 276 supported about a distal portion of the shaft 272. The proximal coupling portion 274 is secured to the proximal end of the elongate pin shaft 272 and is configured to engage an alignment pin driver 31 (FIG. 3) of the stapling device 10 when the cartridge assembly 260 is coupled to the clamp slide assembly 42 (FIG. 3) of the stapling device 10 (FIG. 1). The alignment pin driver 31 is selectively movable to advance the upper alignment pin 270 from a retracted position located within the cartridge body 264 (FIG. 25) to an advanced position received within the upper opening 56 in the staple deforming surface 52 of the anvil assembly 48. For a more detailed description of exemplary aspects of operation and structure of the alignment pin driver 31, see the '508 patent.

Figure 23:
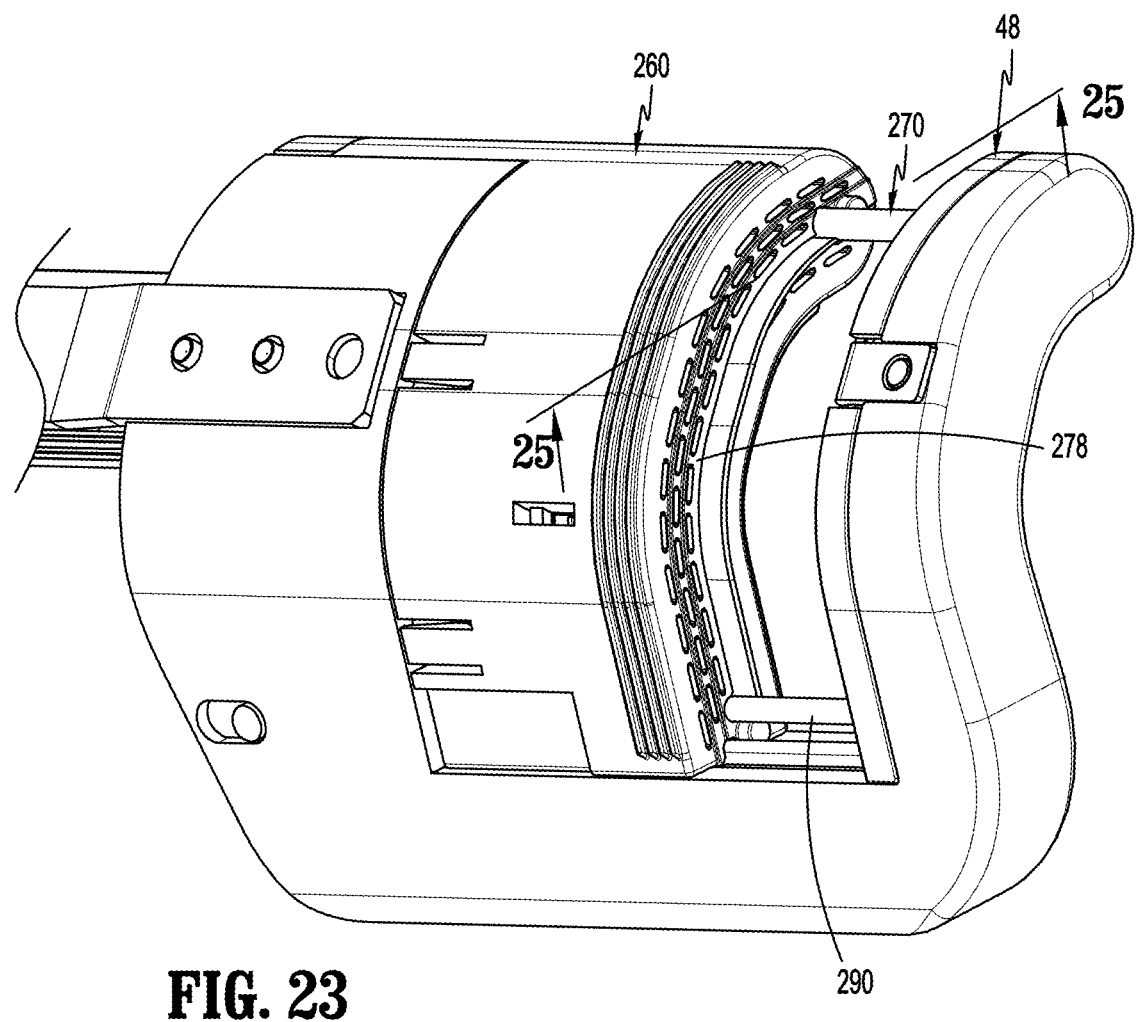
FIG. 23 is a side perspective view of the distal portion of the surgical stapling device shown in FIG. 1 including a cartridge assembly with an alternative version of an upper alignment pin.
Figure 24:
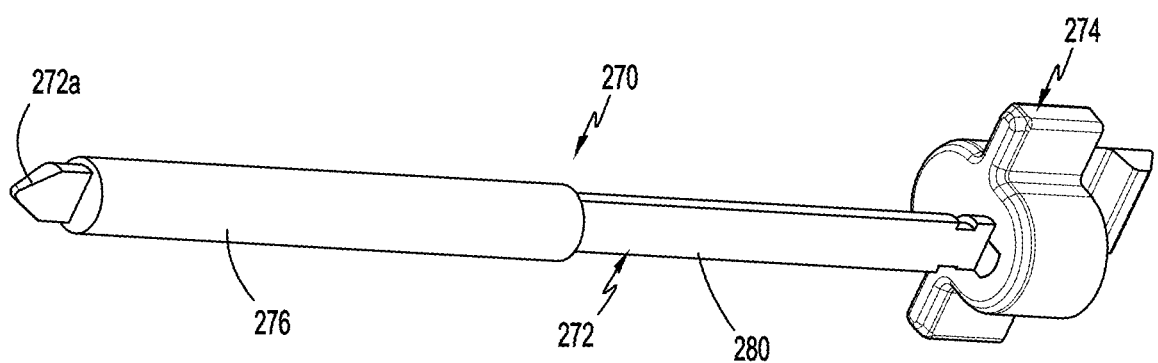
FIG. 24 is a side perspective view of the upper alignment pin of the cartridge assembly shown in FIG. 23.
Figure 26:
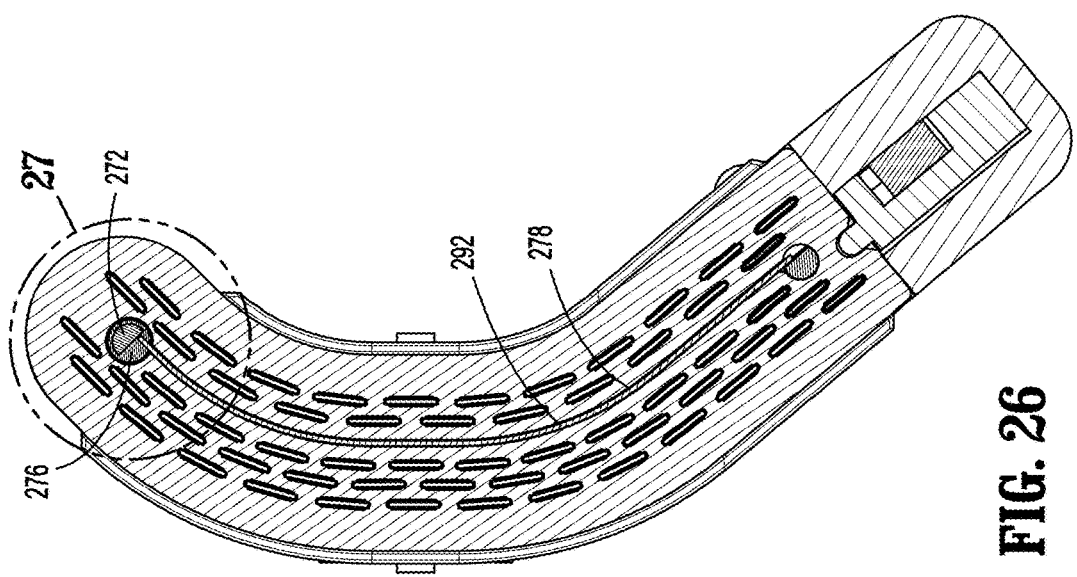
FIG. 26 is a cross-sectional view taken along section line 26-26 of FIG. 25.
Figure 25:
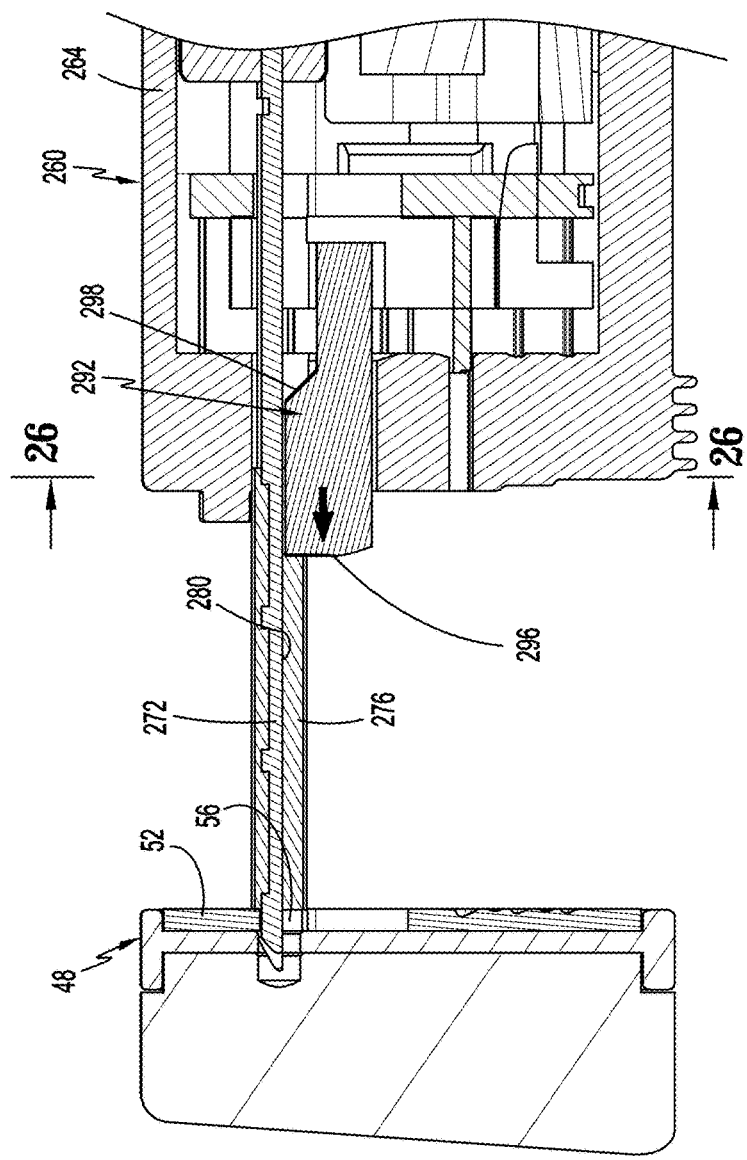
FIG. 25 is a cross-sectional view taken along section line 25-25 of FIG. 23.
Figure 27:
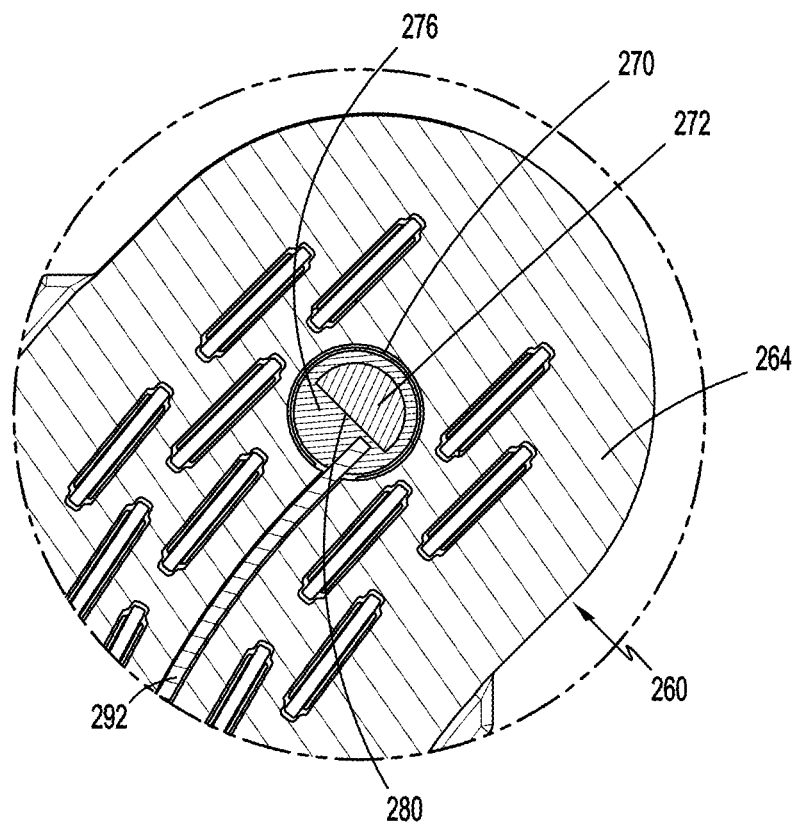
FIG. 27 is an enlarged view of the area of detail shown in FIG. 26.
Figure 28:
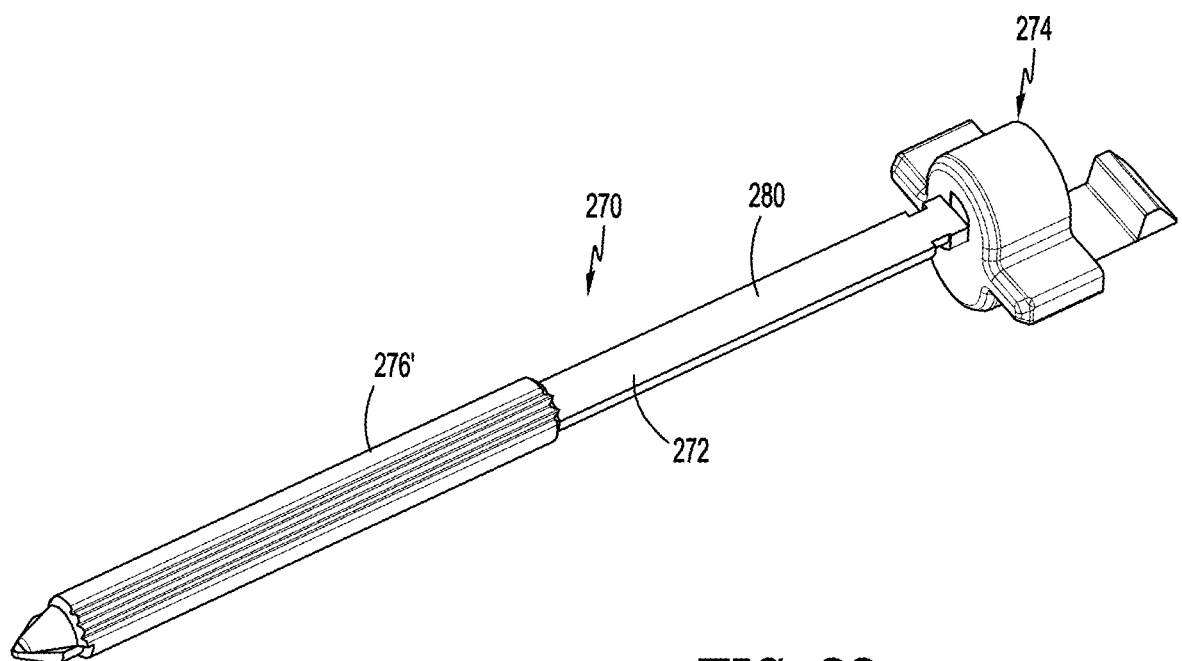
FIG. 28 is another alternative version of the upper alignment pin shown in FIG. 23.
Figure 29:
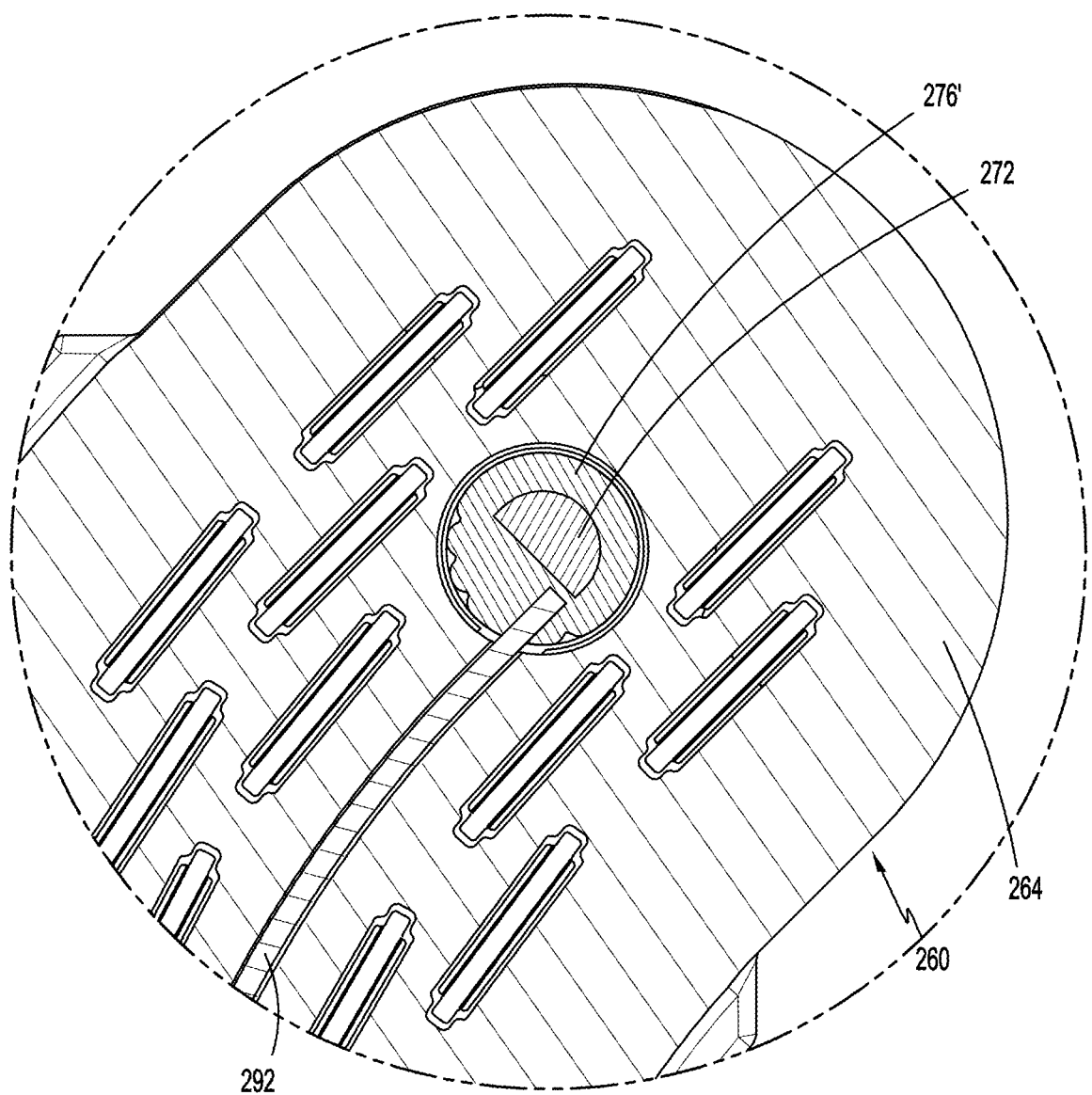
FIG. 29 is a cross-sectional view taken through a cartridge assembly including the upper alignment pin shown in FIG. 28.

In aspects of the disclosure, the elongate pin shaft 272 of the upper alignment pin 270 is formed of metal, e.g., stainless steel, and has a D-shaped cross-sectional shape and a tapered tip 272a. The elongate pin shaft 272 has a flat side 280 that faces inwardly towards the lower alignment pin 290 (FIG. 23). In other aspects of the disclosure, the over mold 276 has a cylindrical configuration and is formed of a suitable polymeric or plastic material such as silicon rubber. Alternately, the use of other materials of construction and other over mold configurations is envisioned. For example, the over mold 276' can have a flower shaped configuration as shown in FIGS. 28 and 29.

The cartridge assembly 260 includes a knife blade 292 (FIG. 25) that is movable between retracted and advanced positions within the cartridge assembly 260 from a position recessed within the cartridge body 264 of the cartridge assembly 260 to a position extending from a knife slot 278 defined by the cartridge body 264 as is known in the art. In the cartridge assembly 260, the knife blade 292 is positioned to move along the flat side 280 of the elongate pin shaft 272 and includes sharp edges 296 and 298 that cut through the over mold 276 as the knife blade 292 is moved towards its advanced position and returned to its retracted position. Supporting tissue on the over mold 276 and advancing the knife blade 292 through the over mold increases the likelihood that tissue positioned adjacent the upper alignment pin will be cleanly cut.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A surgical stapling device comprising:
    an elongate body having a proximal portion and a distal portion;
    a tool assembly supported on the distal portion of the elongate body, the tool assembly including:
        a U-shaped frame having a first transverse portion, a second transverse portion, and a longitudinal portion, the longitudinal portion connecting the first transverse portion to the second transverse portion, the second transverse portion defining at least one longitudinal slot;
        an anvil assembly supported on the first transverse portion of the U-shaped frame, the anvil assembly including staple deforming surface defining a knife slot and a lower opening;
        a reload assembly including:
            a cartridge assembly including a cartridge body defining a cavity, a knife slot, and a plurality of staple pockets, the cartridge assembly further including a tissue engaging surface, a plurality of staples positioned within the staple pockets, and a first alignment pin, the first alignment pin movable from a retracted position positioned within the cartridge body to a fully advanced position extending from the cartridge body and into the lower opening defined in the anvil assembly;
            a shipping cap including a base member, the shipping cap supported on the cartridge body with the base member positioned on the tissue engaging surface of the cartridge body to prevent advancement of the first alignment pin and to retain the plurality of staples within the plurality of staple pockets;
        a clamp slide assembly including a distal portion and a proximal portion, the distal portion defining a distal cartridge support, the clamp slide assembly movable between a retracted position and an advanced position to move the cartridge assembly in relation to the anvil assembly between open and clamped positions; and
        an alignment pin advancement assembly supported on the second transverse portion of the U-shaped frame, the alignment pin advancing assembly including a tube, at least one button, a shaft, and a biasing member, the tube supported within the second transverse portion of the U-shaped frame for movement in relation to the second transverse portion between retracted and advanced positions, the shaft supported within the tube for movement in relation to the tube between retracted and advanced positions, the biasing member positioned within the tube to urge the shaft towards its advanced position, the at least one button extending through the at least one longitudinal slot defined within the second transverse portion of the U-shaped frame and coupled to the tube, the at least one button being movable within the at least one longitudinal slot from a retracted position to an advanced position to move the tube within the second transverse portion between its retracted and advanced positions;
        wherein the shaft is aligned with the first alignment pin to urge the first alignment pin towards its advanced position.

2. The surgical stapling device of claim 1, wherein the at least one longitudinal slot includes two longitudinal slots and the at least one button includes two buttons.

3. The surgical stapling device of claim 1, wherein the shipping cap includes an engagement portion configured to releasably secure the shipping cap to the cartridge assembly, the shipping cap removable from the cartridge assembly to allow the shaft of the alignment pin advancement assembly to advance the first alignment pin from its retracted position to a partially advanced position in which the first alignment pin is spaced from the anvil assembly.

4. The surgical stapling device of claim 3, wherein the at least one button is movable within the at least one longitudinal slot to move the first alignment pin from the partially advanced position to the fully advanced position.

5. The surgical stapling device of claim 4, wherein the at least one longitudinal slot includes spaced protrusions, one of the spaced protrusions positioned to retain the at least one button in its retracted position in the at least one longitudinal slot and the other of the spaced protrusions positioned to retain the button in its advanced position within the at least one longitudinal slot.

6. The surgical stapling device of claim 1, further including a handle assembly, the proximal portion of the elongate body coupled to the handle assembly.

7. The surgical stapling device of claim 1, wherein the distal cartridge support of the clamp slide assembly includes an outer surface that defines at least one guide member, and the cartridge body includes side walls defining the cavity that include at least one longitudinal guide channel that receives the at least one guide member during securement of the cartridge assembly to the distal cartridge support of the clamp slide assembly to properly align the cartridge assembly on the distal cartridge support.

8. The surgical stapling device of claim 7, wherein the at least one guide member includes two guide members positioned on the outer surface of the distal cartridge support on each side of the distal cartridge support, and the at least one longitudinal guide channel includes two longitudinal guide channels defined on each of the side walls of the cartridge body.

9. The surgical stapling device of claim 8, wherein the distal cartridge support of the clamp slide assembly includes at least one detent and the cartridge body defines at least one resilient leg and at least one recess, the at least one resilient leg being deformable out of the path of the at least one detent to allow passage of the at least one detent into the at least one recess to secure the cartridge assembly to the distal cartridge support of the clamp slide assembly.

10. The surgical stapling device of claim 9, wherein the at least one detent includes a plurality of detents, the at least one resilient leg includes a plurality of resilient legs, and the at least one recess includes a plurality of recesses.

11. The surgical stapling device of claim 1, further including a second alignment pin spaced from the first alignment pin, the second alignment pin including an elongate shaft and an over mold supported about the elongate shaft, the second alignment pin movable from a retracted position within the cartridge body to an advanced positon engaged with the anvil assembly.

12. The surgical stapling device of claim 11, wherein the elongate shaft of the second alignment pin is formed from metal and the over mold is formed from of a plastic or polymeric material.

13. The surgical stapling device of claim 12, wherein the over mold is formed from a silicon rubber.

14. A surgical stapling device comprising:
an elongate body having a proximal portion and a distal portion;
a tool assembly supported on the distal portion of the elongate body, the tool assembly including:
a U-shaped frame having a first transverse portion, a second transverse portion, and a longitudinal portion, the longitudinal portion connecting the first transverse portion to the second transverse portion, the second transverse portion defining at least one longitudinal slot;
an anvil assembly supported on the first transverse portion of the U-shaped frame, the anvil assembly including staple deforming surface defining a knife slot and a lower opening;
a cartridge assembly including a cartridge body having side walls with inner surfaces defining a cavity, the inner surfaces of the side walls defining at least one longitudinal channel;
a clamp slide assembly including a distal portion and a proximal portion, the distal portion defining a distal cartridge support, the clamp slide assembly movable between a retracted position and an advanced position to move the cartridge assembly in relation to the anvil assembly between open and clamped positions, the distal cartridge support of the clamp slide assembly having an outer surface that defines at least one guide member, wherein the at least one longitudinal guide channel of the cartridge body receives the at least one guide member of the distal cartridge support during securement of the cartridge assembly to the distal cartridge support of the clamp slide assembly to properly align the cartridge assembly onto the distal cartridge support.

15. The surgical stapling device of claim 14, wherein the at least one guide member includes two guide members positioned on the outer surface of the distal cartridge support on each side of the distal cartridge support, and the at least one longitudinal guide channel includes two longitudinal guide channels defined on each of the side walls of the cartridge body.

16. The surgical stapling device of claim 15, wherein the distal cartridge support of the clamp slide assembly includes at least one detent and the cartridge body defines at least one resilient leg and at least one recess, the at least one resilient leg being deformable out of the path of the at least one detent to allow passage of the at least one detent into the at least one recess to secure the cartridge assembly to the distal cartridge support of the clamp slide assembly.

17. The surgical stapling device of claim 16, wherein the at least one detent includes a plurality of detents, the at least one resilient leg includes a plurality of resilient legs, and the at least one recess includes a plurality of recesses.

18. A surgical stapling device comprising:
an elongate body having a proximal portion and a distal portion;
a tool assembly supported on the distal portion of the elongate body, the tool assembly including:
a U-shaped frame having a first transverse portion, a second transverse portion, and a longitudinal portion, the longitudinal portion connecting the first transverse portion to the second transverse portion;
an anvil assembly supported on the first transverse portion of the U-shaped frame, the anvil assembly including staple deforming surface defining a knife slot and a lower opening;
a cartridge assembly including a cartridge body, a knife blade, and an alignment pin, the alignment pin including an elongate shaft and an over mold supported about the elongate shaft, the alignment pin movable from a retracted position positioned within the cartridge body to an advanced positon engaged with the anvil assembly, the knife blade movable within the cartridge body between a retracted position and an advanced position; and
a clamp slide assembly including a distal portion and a proximal portion, the distal portion defining a distal cartridge support for supporting the cartridge assembly, the clamp slide assembly movable between a retracted position and an advanced position to move the cartridge assembly in relation to the anvil assembly between open and clamped positions.

19. The surgical stapling device of claim 18, wherein the elongate shaft of the alignment pin is formed from metal and the over mold is formed from of a plastic or polymeric material, and the knife blade is positioned to cut through the over mold portion as the knife blade moves between it retracted and advanced positions.

20. The surgical stapling device of claim 19, wherein the over mold is formed from a silicon rubber.

\* \* \* \* \*